(12) United States Patent
Ariki et al.

(10) Patent No.: US 12,392,762 B2
(45) Date of Patent: Aug. 19, 2025

(54) SOIL SENSOR

(71) Applicant: DENSO CORPORATION, Kariya (JP)

(72) Inventors: Tomohide Ariki, Kariya (JP); Kei Shimakura, Kariya (JP)

(73) Assignee: DENSO CORPORATION, Kariya (JP)

( * ) Notice: Subject to any disclaimer, the term of this patent is extended or adjusted under 35 U.S.C. 154(b) by 275 days.

(21) Appl. No.: 18/329,194

(22) Filed: Jun. 5, 2023

(65) Prior Publication Data

US 2023/0314400 A1    Oct. 5, 2023

Related U.S. Application Data

(63) Continuation of application No. PCT/JP2022/003362, filed on Jan. 28, 2022.

(30) Foreign Application Priority Data

Feb. 8, 2021  (JP) .................................. 2021-018324
Feb. 8, 2021  (JP) .................................. 2021-018325
Aug. 16, 2021 (JP) .................................. 2021-132202
Aug. 16, 2021 (JP) .................................. 2021-132203

(51) Int. Cl.
*G01N 33/24* (2006.01)
*G01N 27/04* (2006.01)
*G01N 27/22* (2006.01)

(52) U.S. Cl.
CPC ......... *G01N 33/246* (2013.01); *G01N 27/048* (2013.01); *G01N 27/223* (2013.01)

(58) Field of Classification Search
None
See application file for complete search history.

(56) References Cited

U.S. PATENT DOCUMENTS

| 6,719,488 B2 * | 4/2004 | Kuroda | G01N 33/245 |
| | | | 405/36 |
| 7,042,234 B2 * | 5/2006 | Buss | G01N 33/246 |
| | | | 324/658 |
| 7,219,024 B2 * | 5/2007 | Gamache | G01N 27/028 |
| | | | 702/182 |

FOREIGN PATENT DOCUMENTS

JP   2005-156263 A   6/2005
JP   2017-151042 A   8/2017

* cited by examiner

*Primary Examiner* — Eman A Alkafawi
*Assistant Examiner* — Suresh K Rajaputra
(74) *Attorney, Agent, or Firm* — POSZ LAW GROUP, PLC

(57) ABSTRACT

A soil sensor includes a base, a first detection unit, a second detection unit, and a circuit unit. A first signal line of the first detection unit has a circular wiring pattern when being projected to an installation surface of the base. A first GND line of the first detection unit is arranged to be spaced from the first signal line and has a wiring pattern, when being projected to the installation surface, located within a region surrounded by the wiring pattern of the first signal line projected on the installation surface. The second detection unit is located within a region surrounded by the wiring pattern of the first GND line projected on the installation surface of the base.

32 Claims, 23 Drawing Sheets

II-II CROSS-SECTIONAL VIEW

VIII-VIII CROSS-SECTIONAL VIEW

XXXV-XXXV CROSS-SECTIONAL VIEW

SOIL SENSOR

CROSS REFERENCE TO RELATED APPLICATION

The present application is a continuation application of International Patent Application No. PCT/JP2022/003362 filed on Jan. 28, 2022, which designated the U.S. and claims the benefit of priority from Japanese Patent Application No. 2021-18325 filed on Feb. 8, 2021, Japanese Patent Application No. 2021-18324 filed on Feb. 8, 2021, Japanese Patent Application No. 2021-132203 filed on Aug. 16, 2021, and Japanese Patent Application No. 2021-132202 filed on Aug. 16, 2021. The entire disclosures of all of the above applications are incorporated herein by reference.

TECHNICAL FIELD

The present disclosure relates to a soil sensor.

BACKGROUND ART

A soil sensor that measures a water content of soil includes a folded transmission path and a circuit unit. The folded transmission path includes a first linear portion and a second linear portion arranged in parallel with each other, a folded portion integrating respective one end sides of the linear portions, and a linear conductor arranged between and in parallel with the linear portions.

SUMMARY

According to an aspect of the present disclosure, a soil sensor includes a base, a first detection unit, a second detection unit, and a circuit unit. The base has an installation surface. The first detection unit includes a first signal line and a first GND line arranged on the base. The second detection unit includes a second signal line, a second GND line and a ceramic body arranged on the installation surface of the base. The second signal line has one end portion that is one electrode with respect to the ceramic body, and the second GND line has one end portion that is another electrode with respect to the ceramic body. The circuit unit inputs a frequency signal between the one end portion of the first signal line and the one end portion of the first GND line. The circuit unit measures a water potential of soil based on capacitance between the one end portion of the second signal line and the one end portion of the second GND line, the capacitance being changed by water contained in the soil entering the ceramic body. The first signal line has a circular wiring pattern when being projected on the installation surface of the base. The first GND line is arranged to be spaced from the first signal line, and has a wiring pattern, when being projected on the installation surface of the base, within a region surrounded by the wiring pattern of the first signal line projected on the installation surface. The second detection unit is located within a region surrounded by the wiring pattern of the first GND line projected on the installation surface of the base.

BRIEF DESCRIPTION OF DRAWINGS

The above and other objects, features, and advantages of the present disclosure will become more apparent from the following detailed description with reference to the accompanying drawings. In the accompanying drawings.

DESCRIPTION OF EMBODIMENTS

Figure 1:
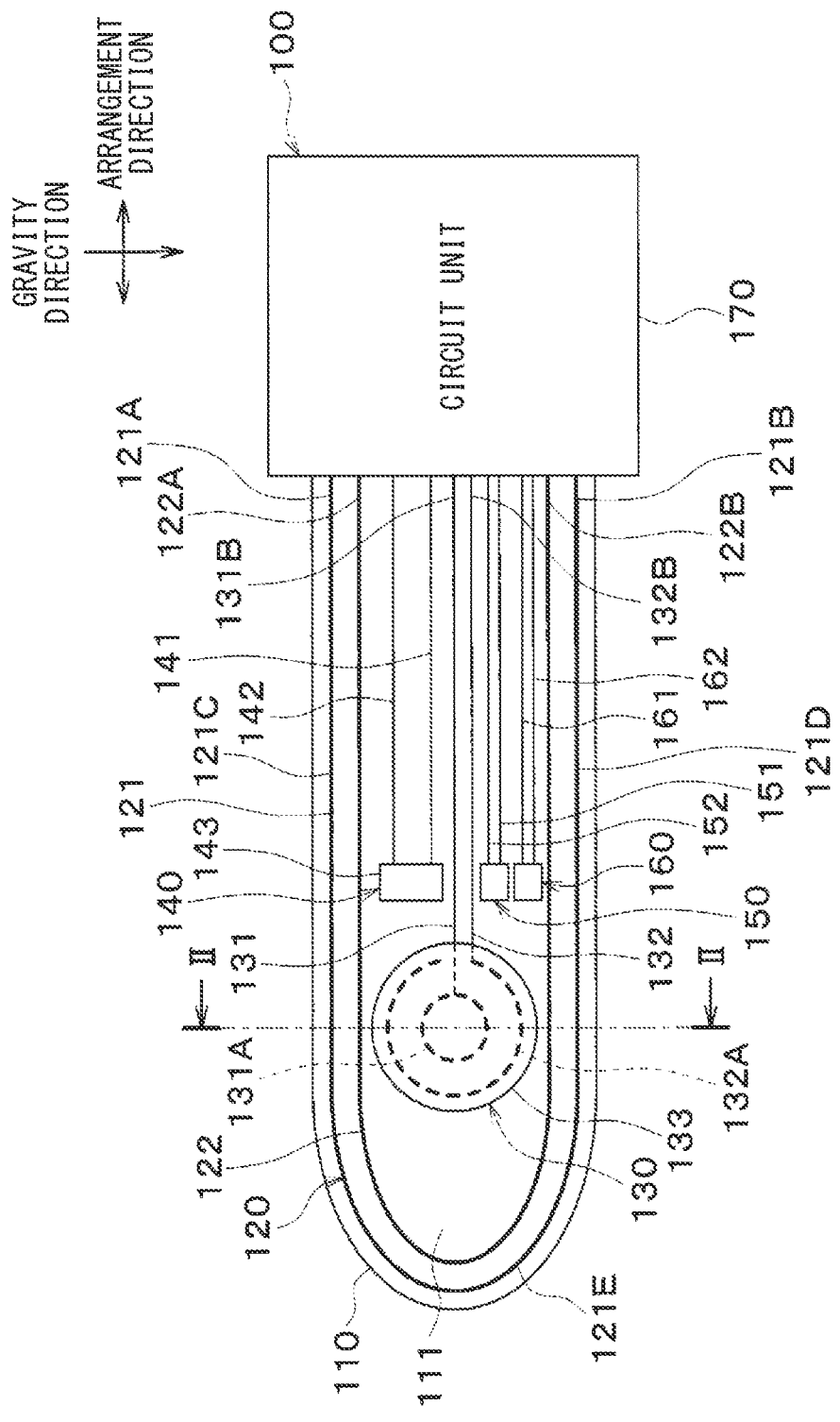
FIG. 1 is a plan view of a soil sensor according to a first embodiment.

A conventional device that measures a water content of soil includes a folded transmission path and a circuit unit.

The folded transmission path includes a first linear portion and a second linear portion arranged in parallel with each other, a folded portion integrating respective one end sides of the linear portions, and a linear conductor arranged between and in parallel with the linear portions.

The circuit unit supplies a frequency signal having a predetermined frequency to the folded transmission path and obtains the permittivity of the soil based on a frequency signal from the folded transmission path. The circuit unit obtains the water content of the soil by using the information of the permittivity.

In addition to the above conventional technique, devices are known each of which measures a water potential of soil. Although each device can measure a water content or a water potential, each device has difficulty simultaneously measuring the water content and the water potential.

Consideration may be thus given to integration of a device that measures a water content and a device that measures a water potential. In a case where the integration is made, a detection unit that measures a water content and a detection unit that measures a water potential are arranged close to each other in order to measure the same position in soil. This is because a large difference may be present in the state of the soil if the position to be measured is slightly shifted in the soil.

However, closer arrangement of the detection units may generate unnecessary capacitance. One of the detection units may thus have an influence on the other detection unit. Such a possibility is not limited to the case of integrating the device that measures a water content and the device that measures a water potential, and may be applied to a case of detecting at least two physical quantities. For example, even when a device that measures electric conductivity and the device that measures a water potential are integrated, one of the detection units may have an influence on the other detection unit.

An object of the present disclosure is to provide a soil sensor that can reduce mutual influence between at least two detection units.

According to a first aspect of the present disclosure, a soil sensor includes a base, a first detection unit, a second detection unit, and a circuit unit.

The base has an installation surface. The first detection unit includes a first signal line and a first GND line arranged on the base. The second detection unit includes a second signal line, a second GND line and a ceramic body arranged on the installation surface of the base. The second signal line has one end portion that is one electrode with respect to the ceramic body, and the second GND line has one end portion that is another electrode with respect to the ceramic body.

The circuit unit inputs a frequency signal between the one end portion of the first signal line and the one end portion of the first GND line, and obtains water content of soil on which the base is arranged, based on a propagation time taken for the frequency signal to reach another end portion of the first signal line. The circuit unit measures a water potential of soil based on capacitance between the one end portion of the second signal line and the one end portion of the second GND line, the capacitance being changed by water contained in the soil entering the ceramic body.

The first signal line has a circular wiring pattern when being projected on the installation surface of the base. The first GND line is arranged to be spaced from the first signal line, and has a wiring pattern, when being projected on the installation surface of the base, within a region surrounded by the wiring pattern of the first signal line projected on the installation surface.

The second detection unit is located within a region surrounded by the wiring pattern of the first GND line projected on the installation surface of the base.

Thus, the second detection unit is arranged while the second detection unit avoids the region of an electric field spread by the first signal line and the first GND line of the first detection unit. Therefore, mutual influence can be reduced between the first detection unit configured to measure the water content of the soil and the second detection unit configured to measure the water potential of the soil.

According to a second aspect of the present disclosure, a soil sensor includes a base, a first detection unit, a second detection unit, and a circuit unit.

The base has an installation surface. The first detection unit includes a first signal line and a first GND line arranged on the base. The second detection unit includes a second signal line, a second GND line and a ceramic body arranged on the installation surface of the base. The second signal line has one end portion that is one electrode with respect to the ceramic body, and the second GND line has one end portion that is another electrode with respect to the ceramic body.

The circuit unit inputs a frequency signal between one end portion of the first signal line and one end portion of the first GND line, and obtains electric conductivity of soil, on which the base is arranged, based on steepness of a slope of a rise of the frequency signal reaching another end portion of the first signal line. The circuit unit measures a water potential of soil based on capacitance between the one end portion of the second signal line and the one end portion of the second GND line, the capacitance being changed by water contained in the soil entering the ceramic body.

The first signal line has a circular wiring pattern when being projected on the installation surface of the base. The first GND line is arranged to be spaced from the first signal line, and has a wiring pattern, when being projected on the installation surface of the base, located within a region surrounded by the wiring pattern of the first signal line projected on the installation surface.

The second detection unit is located within a region surrounded by the wiring pattern of the first GND line projected on the installation surface of the base.

Thus, the second detection unit is arranged while the second detection unit avoids the region of an electric field spread by the first signal line and the first GND line of the first detection unit. Therefore, mutual influence can be reduced between the first detection unit configured to measure the electric conductivity of the soil and the second detection unit configured to measure the water potential of the soil.

Embodiments of the present disclosure will be described hereafter referring to drawings. In the embodiments, a part that corresponds to a matter described in a preceding embodiment may be assigned with the same reference numeral, and redundant explanation for the part may be omitted. When only a part of a configuration is described in an embodiment, another preceding embodiment may be applied to the other parts of the configuration. The parts may be combined even if it is not explicitly described that the parts can be combined. The embodiments may be partially combined even if it is not explicitly described that the embodiments can be combined, provided there is no harm in the combination.

First Embodiment

Hereinafter, a first embodiment will be described with reference to the drawings. A soil sensor according to the present embodiment is a sensor that detects physical quantities related to soil. The soil is a foundation for growing crops, and includes earth, sand, and clay.

As illustrated in FIG. 1, a soil sensor 100 includes a base 110, a first detection unit 120, a second detection unit 130, a third detection unit 140, a fourth detection unit 150, a fifth detection unit 160, and a circuit unit 170.

The base 110 is a component to which each of the detection units 120 to 160 is installed. The base 110 is, for example, a printed circuit board having one surface 111. The base 110 may be a flexible substrate. The base 110 has, for example, a rectangular parallelepiped shape. For example, one end side of the base 110 is formed in an arc shape. The other end side of the base 110 is integrated with the circuit unit 170. Alternatively, the other end side of the base 110 is inserted into the circuit unit 170. The base 110 has a shape formed along an arrangement direction, when a direction in which the base 110 and the circuit unit 170 are aligned is defined as the arrangement direction.

The first detection unit 120 is a component for measuring the water content of the soil and the electric conductivity of the soil. The water content is the ratio of water contained in the soil. That is, the water content is the volume water content of the soil. The water content is expressed in units of, for example, percent (%). The electric conductivity is a physical quantity corresponding to the salinity concentration of the soil.

The first detection unit 120 includes a first signal line 121 and a first ground (GND) line 122. The first signal line 121 and the first GND line 122 are arranged on the one surface 111 of the base 110. Each of the first signal line 121 and the first GND line 122 is metal wiring formed of Cu or the like.

The first signal line 121 is a wiring pattern arranged on an outer edge portion of the one surface 111 of the base 110. The first signal line 121 is arranged along the outline of the one surface 111 of the base 110 such that one end portion 121A and the other end portion 121B of the first signal line 121 are positioned on the other end side of the one surface 111 of the base 110.

Specifically, the first signal line 121 includes a wiring pattern projected on the one surface 111 of the base 110, and this wiring pattern is a circular wiring pattern. In the present embodiment, the first signal line 121 is arranged on the one surface 111 of the base 110. The wiring pattern of the first signal line 121 projected on the one surface 111 of the base 110 and the actual wiring pattern of the first signal line 121 can be thus regarded as identical. The wiring pattern of the first signal line 121 projected on the one surface 111 of the base 110 includes a first straight portion 121C, a second straight portion 121D, and a connection portion 121E. The second straight portion 121D is arranged in parallel with the first straight portion 121C. In the present embodiment, the first straight portion 121C and the second straight portion 121D are arranged in parallel. In addition to the parallel arrangement with the first straight portion 121C, the second straight portion 121D may be arranged to be slightly inclined with respect to the first straight portion 121C. A side of the first straight portion 121C opposite to the connection portion 121E corresponds to the one end portion 121A of the first signal line 121. A side of the second straight portion 121D opposite to the connection portion 121E corresponds to the other end portion 121B of the first signal line 121. The connection portion 121E is arranged in an arc shape along the outline of the one end side of the base 110. The one end portion 121A and the other end portion 121B of the first signal line 121 are electrically connected to the circuit unit 170.

The first GND line 122 is a wiring pattern arranged inward of the first signal line 121 on the one surface 111 of the base 110. That is, the wiring pattern of the first GND line 122 projected on the one surface 111 of the base 110 is arranged within a region surrounded by the first signal line 121 projected on the one surface 111 of the base 110. The surrounded region is a region wholly surrounded when a portion corresponding to the one end portion 121A of the first signal line 121 and a portion corresponding to the other end portion 121B of the first signal line 121 are connected by an imaginary line, within the one surface 111 of the base 110. In the present embodiment, the first GND line 122 is arranged on the one surface 111 of the base 110. The wiring pattern of the first GND line 122 projected on the one surface 111 of the base 110 and the actual wiring pattern of the first GND line 122 can be thus regarded as identical. The first GND line 122 is arranged to be spaced from the first signal line 121 at a first interval.

The first GND line 122 is arranged circularly along the first signal line 121 such that one end portion 122A and the other end portion 122B of the first GND line 122 are positioned on the other end side of the one surface 111 of the base 110. That is, the first GND line 122 is a wiring pattern having a form identical to that of the first signal line 121. The first interval need not have a constant value at every location between the first signal line 121 and the first GND line 122. The one end portion 122A and the other end portion 122B of the first GND line 122 are electrically connected to the circuit unit 170.

Figure 2:
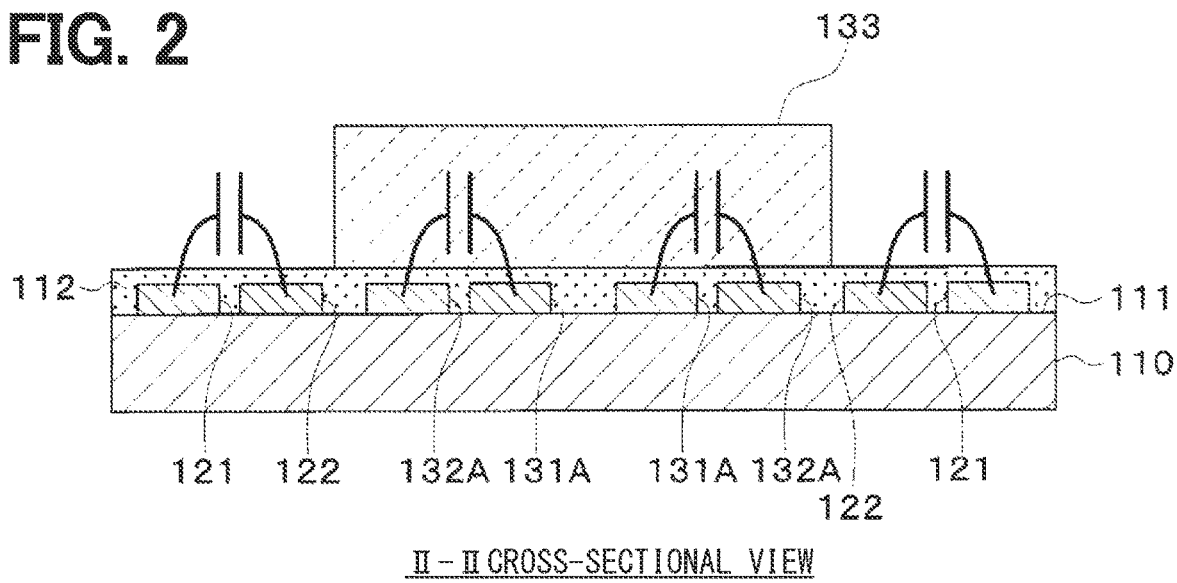
FIG. 2 is a cross-sectional view taken along line II-II of FIG. 1.

As illustrated in FIG. 2, the first signal line 121 and the first GND line 122 are covered with an insulating film 112. The insulating film 112 is a protective film that protects the first signal line 121 and the first GND line 122 from corrosion. In FIG. 1, the illustration of the insulating film 112 is omitted.

The second detection unit 130 is a component for measuring the water potential of the soil. The water potential is a physical quantity corresponding to the pressure of water contained in the soil. The water potential is expressed in units of, for example, pascal (Pa). The second detection unit 130 is arranged inward of the first GND line 122. That is, the second detection unit 130 is arranged within a region surrounded by the wiring pattern of the first GND line 122 projected on the one surface 111 of the base 110.

As illustrated in FIG. 1, the second detection unit 130 includes a second signal line 131, a second GND line 132, and a ceramic body 133. The second signal line 131 and the second GND line 132 are arranged on the one surface 111 of the base 110. Each of the second signal line 131 and the second GND line 132 is metal wiring formed of Cu or the like.

Each of the second signal line 131 and the second GND line 132 is a wiring pattern linearly arranged from the other end side to the one end side of the one surface 111 of the base 110. That is, the second signal line 131 has one end portion 131A, which is positioned on the one end side of the one surface 111 of the base 110, and has the other end portion 131B, which is positioned on the other end side of the one surface 111 of the base 110. Similarly, the second GND line 132 has one end portion 132A, which is positioned on the one end side of the one surface 111 of the base 110, and has the other end portion 132B, which is positioned on the other end side of the one surface 111 of the base 110. The one end portion 131A of the second signal line 131 is one electrode with respect to the ceramic body 133.

The one end portion 132A of the second GND line 132 is arranged to be spaced from the one end portion 131A of the second signal line 131 at a second interval, and is a pattern surrounding the one end portion 131A of the second signal line 131. For example, the one end portion 131A of the second signal line 131 is an annular wiring pattern. The one end portion 132A of the second GND line 132 is an annular pattern that surrounds the one end portion 131A of the second signal line 131 while contact is avoided between the one end portion 131A of the second signal line 131 and the one end portion 132A of the second GND line 132. As illustrated in FIG. 2, the second signal line 131 and the second GND line 132 are covered with the insulating film 112. The one end portion 132A of the second GND line 132 is the other electrode with respect to the ceramic body 133.

The ceramic body 133 is arranged above the one end portion 131A of the second signal line 131 and the one end portion 132A of the second GND line 132. Specifically, the ceramic body 133 is positioned above the one end portion 131A of the second signal line 131 and the one end portion 132A of the second GND line 132 by being arranged on the insulating film 112.

For example, cordierite or alumina can be used for the ceramic body 133. The permittivity of cordierite is 4, and the permittivity of alumina is 9.6. The ceramic body 133 has a cylindrical shape in accordance with the wiring pattern of the one end portion 131A of the second signal line 131 and the wiring pattern of the one end portion 132A of the second GND line 132. For example, when each of the wiring pattern of the one end portion 131A of the second signal line 131 and the wiring pattern of the one end portion 132A of the second GND line 132 has a quadrilateral annular pattern, the ceramic body 133 has a rectangular parallelepiped shape.

As illustrated in FIG. 1, the third detection unit 140 is a component for measuring the temperature of the soil. The third detection unit 140 is arranged inward of the first GND line 122 projected on the one surface 111, within the one surface 111 of the base 110, and is arranged in a region where the second detection unit 130 is not arranged.

The third detection unit 140 includes a third signal line 141, a third GND line 142, and a thermistor 143. Each of the third signal line 141 and the third GND line 142 is metal wiring formed of Cu or the like. The third signal line 141 and the third GND line 142 are covered with the insulating film 112, and are electrically connected to the circuit unit 170.

Each of the third signal line 141 and the third GND line 142 is a wiring pattern linearly arranged from the other end side to the one end side of the one surface 111 of the base 110. The third GND line 142 is arranged adjacent to the first GND line 122. The third signal line 141 is arranged adjacent to one side of the third GND line 142 opposite to the other side thereof adjacent to the first GND line 122. That is, the third signal line 141 is arranged between the third GND line 142 and the second signal line 131.

The thermistor 143 is an element for detecting the temperature of the soil. The thermistor 143 is arranged on the insulating film 112. The thermistor 143 is electrically connected to the third signal line 141 and the third GND line 142 through openings (not illustrated) formed in the insulating film 112. The element for detecting the temperature may be a thermocouple.

The fourth detection unit 150 is a component for detecting the pH of the soil. The fourth detection unit 150 is arranged inward of the first GND line 122 projected on the one surface 111, within the one surface 111 of the base 110, and is arranged in a region where the second detection unit 130 and the third detection unit 140 are not arranged.

The fourth detection unit 150 includes a fourth signal line 151, a fourth GND line 152, and a pair of electrodes (not illustrated). Each of the fourth signal line 151 and the fourth GND line 152 is metal wiring formed of Cu or the like. The fourth signal line 151 and the fourth GND line 152 are covered with the insulating film 112, and are electrically connected to the circuit unit 170.

Each of the fourth signal line 151 and the fourth GND line 152 is a wiring pattern linearly arranged from the other end side to the one end side of the one surface 111 of the base 110. The fourth GND line 152 is arranged adjacent to one side of the second GND line 132 opposite to the other side thereof adjacent to the second signal line 131. The fourth signal line 151 is arranged adjacent to one side of the fourth GND line 152 opposite to the other side thereof adjacent to the second GND line 132. That is, the fourth GND line 152 is arranged between the second GND line 132 and the fourth signal line 151.

The fourth detection unit 150 detects a potential difference between the pair of electrodes caused along with adhesion of water contained in the soil to one of the pair of electrodes. The pair of electrodes are, for example, an ion-sensitive field-effect transistor (ISFET) electrode and a comparison electrode.

The fifth detection unit 160 is a component for detecting the redox potential of the soil. The redox potential or oxidation-reduction potential (ORP) is a physical quantity expressing the degree of oxidation-reduction of the soil. The redox potential may also be expressed as Eh. When the redox potential is positive, oxygen exists in the soil, that is, the soil is in an oxidized state. When the redox potential is negative, no oxygen exists in the soil, that is, the soil is in a reduced state.

For example, reduction proceeds by filling a paddy field with water, and the reduction further proceeds by consuming oxygen when organic substances are decomposed. The soil chemical-reduction sterilization can make the soil oxygen-free by applying an organic substance such as rice bran, bran, or molasses, which is a reducing material, into the soil, and can remove diseases and pests. The state of oxygen-free in the soil is an oxygen-deprived state, a reduced state, or a state in which the redox potential is negative.

The fifth detection unit 160 is arranged inward of the first GND line 122 projected on the one surface 111, within the one surface 111 of the base 110, and is arranged in a region where the second detection unit 130, the third detection unit 140, and the fourth detection unit 150 are not arranged.

The fifth detection unit 160 includes a fifth signal line 161, a fifth GND line 162, and a pair of electrodes (not illustrated). Each of the fifth signal line 161 and the fifth GND line 162 is metal wiring formed of Cu or the like. The fifth signal line 161 and the fifth GND line 162 are covered with the insulating film 112, and are electrically connected to the circuit unit 170.

Each of the fifth signal line 161 and the fifth GND line 162 is a wiring pattern linearly arranged from the other end side to the one end side of the one surface 111 of the base 110. The fifth GND line 162 is arranged adjacent to the first GND line 122. The fifth signal line 161 is arranged between the fifth GND line 162 and the fourth signal line 151.

The fifth detection unit 160 includes a detection electrode and a reference electrode as the pair of electrodes. The fifth detection unit 160 detects a potential difference between the detection electrode and the reference electrode caused along with adhesion of water contained in the soil to the detection electrode.

The circuit unit 170 obtains the water content of the soil, the water potential of the soil, the electric conductivity of the soil, the temperature of the soil, the pH of the soil, and the redox potential of the soil, based on the detection results from the detection units 120 to 160.

The circuit unit 170 includes electronic components such as a microcomputer and an integrated circuit (IC) for controlling each of the detection units 120 to 160. The electronic components are mounted on a printed circuit board dedicated to the circuit unit 170. Alternatively, the electronic components are mounted on the other end side of the base 110. That is, the base 110 may form a part of the circuit unit 170.

The description has been made for the overall configuration of the soil sensor 100 according to the present embodiment. Portions of the base 110 unrelated to sensing may be covered with a coating film. The portions covered with the coating film is thus protected. Alternatively, corrosion of the metal portion is reduced.

Figure 3:
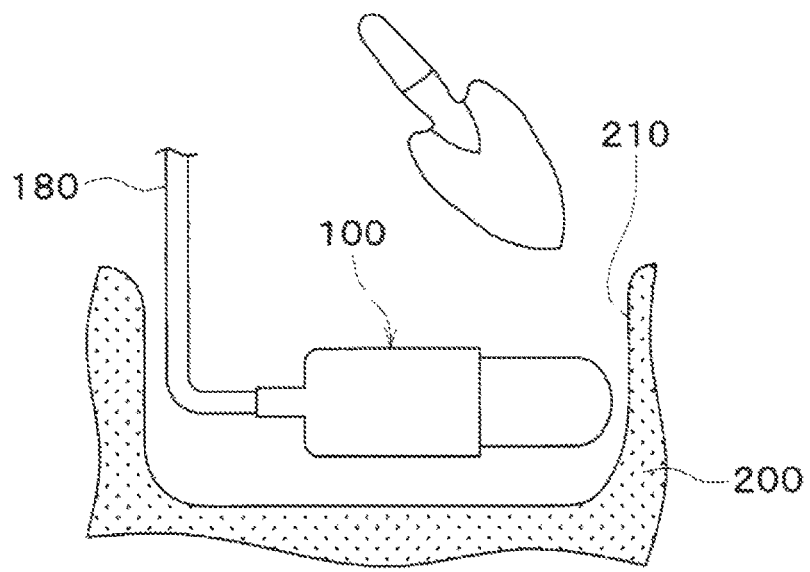
FIG. 3 is a view illustrating arrangement of the soil sensor into soil.

As illustrated in FIG. 3, the soil sensor 100 is arranged in a hole 210 provided in soil 200. The soil sensor 100 is then buried in the soil 200. The soil sensor 100 includes a line 180 connected to the circuit unit 170. The soil sensor 100 receives power from a power supply, outputs a detection signal, and performs other operations, through the line 180.

The soil sensor 100 is arranged such that the arrangement direction is perpendicular to the gravity direction. That is, the base 110 and the circuit unit 170 are arranged along a direction perpendicular to the gravity direction. The soil sensor 100 may not be arranged strictly perpendicular to the gravity direction in terms of the arrangement direction thereof. The arrangement may be acceptable as long as the soil sensor 100 is arranged to be laid down with respect to the gravity direction.

Figure 4:
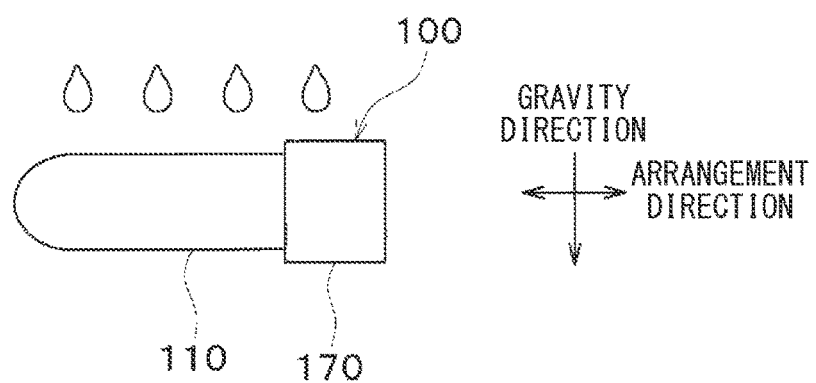
FIG. 4 is a view illustrating a state of raindrops when a base and a circuit unit of the soil sensor are arranged in a direction perpendicular to a gravity direction.
Figure 5:
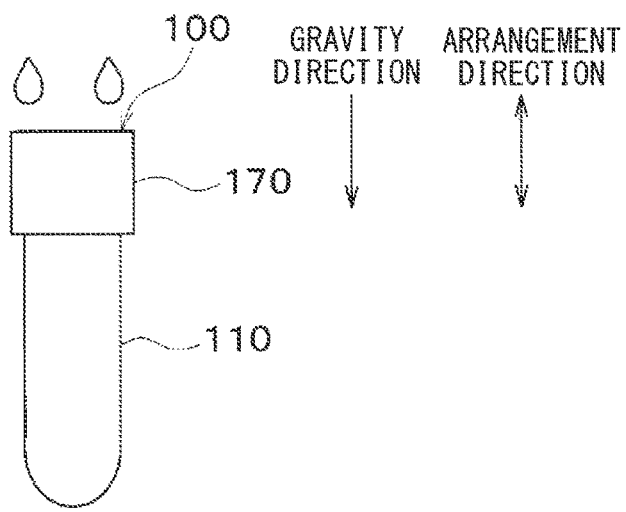
FIG. 5 is a view illustrating a state of raindrops when the base and the circuit unit of the soil sensor are arranged in the gravity direction.

This arrangement allows raindrops to be easily guided to the base 110 of the soil sensor 100 as illustrated in FIG. 4, in a case of rain. In contrast, a case may exist in which the soil sensor 100 is arranged such that the arrangement direction is along the gravity direction, as illustrated in FIG. 5. That is, a case may exist in which the soil sensor 100 is arranged upright along the gravity direction. In such a case, the movement of raindrops is restricted by the circuit unit 170.

A method will be described for obtaining the water content of the soil 200, the electric conductivity of the soil 200, the water potential of the soil 200, the temperature of the soil 200, the pH of the soil 200, and the redox potential of the soil 200.

Figure 6:
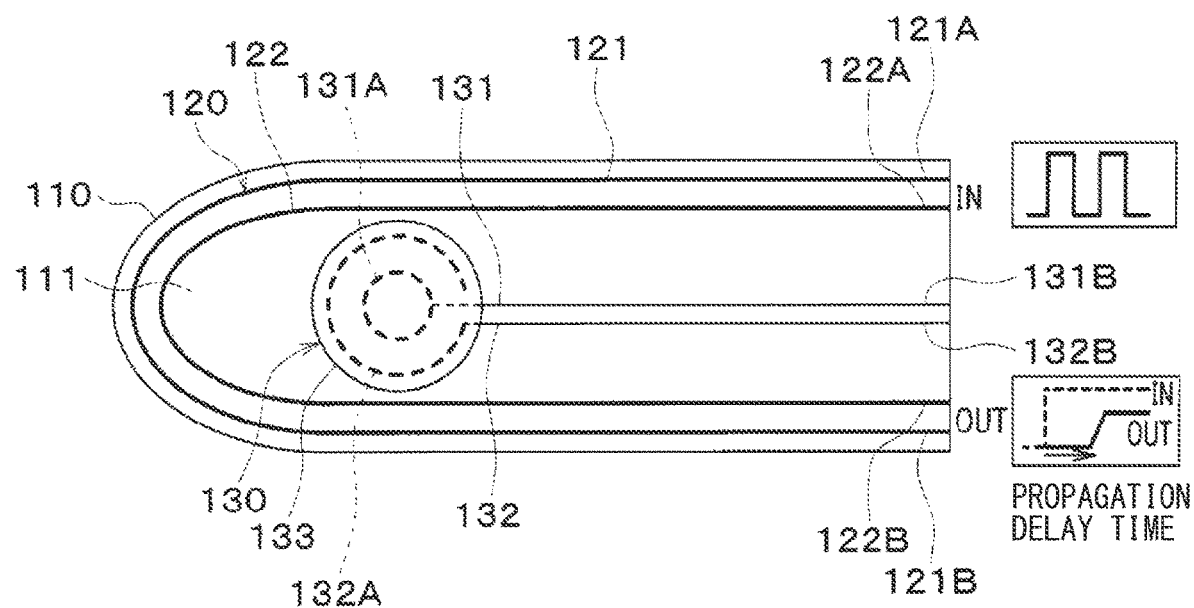
FIG. 6 is a view for explaining a method of measuring a water content.

The first detection unit 120 and the circuit unit 170 measure the water content of the soil 200, based on, for example, time domain transmission. As illustrated in FIG. 6, the circuit unit 170 inputs a frequency signal between the one end portion 121A of the first signal line 121 and the one end portion 122A of the first GND line 122, of the first detection unit 120. In FIG. 6, the illustration of the third to fifth detection units 140 to 160 is omitted.

The frequency signal is, for example, a pulse wave. Delay occurs in a propagation time of the frequency signal due to presence of the soil 200 and water contained in the soil 200. The permittivity of the soil 200 is, for example, ±4, and the permittivity of water is, for example, 80. As illustrated in FIG. 2, a change in permittivity between the first signal line 121 and the first GND line 122 leads to a change in capacitance, and delay occurs in the propagation time of the frequency signal. As illustrated in FIG. 6, the circuit unit 170 measures a propagation time taken for the frequency signal to reach the other end portion 121B of the first signal line 121.

Specifically, the relative permittivity $\varepsilon r$ of water is determined by the water content of the soil 200. Apparent permittivity $\varepsilon a$ around the first detection unit 120 is determined in accordance with the relative permittivity $\varepsilon r$ of water. When the speed of light is denoted by c, the propagation time is denoted by tm, and the pattern length of the first signal line 121 is denoted by Lp, the apparent permittivity $\varepsilon a$ is expressed as $\varepsilon a = (c \times tm/Lp)^2$. The apparent permittivity $\varepsilon a$ is obtained by measuring the propagation time. The relative permittivity $\varepsilon r$ of water is obtained from the apparent permittivity $\varepsilon a$. The water content of the soil 200 is therefore obtained from the relative permittivity $\varepsilon r$ of water.

The first detection unit 120 and the circuit unit 170 measure the electric conductivity of the soil 200, based on the steepness of the slope of the rise of the frequency signal reaching the other end portion 121B of the first signal line 121. As illustrated in FIG. 6, the rise of the frequency signal reaching the circuit unit 170 is inclined in accordance with the electric conductivity of the soil 200. The amplitude of the frequency signal reaching the circuit unit 170 also changes in accordance with the electric conductivity of the soil 200.

When the electric conductivity is high, the slope of the rise of the frequency signal reaching the circuit unit 170 becomes more gradual. That is, a longer time is required until the amplitude of the frequency signal becomes maximum. When the electric conductivity is high, the amplitude of the frequency signal reaching the circuit unit 170 becomes smaller.

In contrast, when the electric conductivity is low, the slope of the rise of the frequency signal reaching the circuit unit 170 becomes steeper. That is, a shorter time is taken until the amplitude of the frequency signal becomes maximum. When the electric conductivity is low, the amplitude of the frequency signal reaching the circuit unit 170 becomes large.

The circuit unit 170 thus converts the slope of the rise of the frequency signal reaching the circuit unit 170 into the electric conductivity of the soil 200. Alternatively, the circuit unit 170 converts the amplitude of the frequency signal reaching the circuit unit 170 into the electric conductivity of the soil 200. Alternatively, the circuit unit 170 converts both the slope of the rise and the maximum amplitude of the frequency signal reaching the circuit unit 170 into the electric conductivity of the soil 200.

The second detection unit 130 and the circuit unit 170 measure the water potential of the soil 200, based on capacitance between the one end portion 131A of the second signal line 131 and the one end portion 132A of the second GND line 132. The second detection unit 130 uses the ceramic body 133 as a substitute to determine water absorbency from the soil 200, that is, water potential. When water contained in the soil 200 enters the ceramic body 133, the permittivity changes. As a result, as illustrated in FIG. 2, capacitance between the second signal line 131 and the second GND line 132 changes.

Specifically, a water absorption rate when water enters the ceramic body 133 is determined in accordance with the water potential of the soil 200. With this relationship, since the relative permittivity εr when the water enters the ceramic body 133 is determined, the capacitance corresponding to the relative permittivity εr is determined. The water potential of the soil 200 is therefore obtained by converting the capacitance into the water potential. For example, when the water potential is denoted by φ and the capacitance is denoted by pF, the capacitance pF is expressed as pF=$\log_{10}$ (−10.2×φ), and the water potential φ is expressed as φ=$10^{pF}$/(−10.2).

The third detection unit 140 and the circuit unit 170 measure the temperature of the soil 200 by using the thermistor 143. The circuit unit 170 obtains the temperature of the soil 200, based on the detection result from the thermistor.

The fourth detection unit 150 and the circuit unit 170 measure the pH of the soil 200, based on the potential difference between the pair of electrodes. For example, the pair of electrodes includes a semiconductor element such as an ISFET electrode, in a semiconductor electrode type. The circuit unit 170 converts a potential difference generated between the ISFET electrode and the comparison electrode into pH by using impedance conversion. A glass electrode type or a metal electrode type may also be used.

The fifth detection unit 160 and the circuit unit 170 measure the redox potential of the soil 200, based on the potential difference between the detection electrode and the reference electrode. The detection electrode is, for example, a platinum electrode. The circuit unit 170 obtains the voltage of the comparison electrode with respect to the platinum electrode, as the redox potential of the soil 200.

For example, when the value of +200 mV is defined as a boundary between oxidation and reduction, the range from +400 mV to +700 mV is defined as an oxidized state, and the range from −250 mV to −300 mV is defined as a reduced state. A dry paddy field is in an oxidized state having a value of, for example, +600 mV.

The circuit unit 170 outputs each of the above physical quantities to an external device. Data obtained with the soil sensor 100 is used for an irrigation system, fertilizer application, and the like. In the irrigation system, a watering amount is adjusted based on information of the water content, the water potential, and the temperature. In the fertilizer application, the amount and components of a fertilizer are adjusted based on the information of the electric conductivity, the pH, and the redox potential.

As described above, in the present embodiment, the second to fifth detection units 130 to 160 are arranged inward of the first GND line 122 of the first detection unit 120. That is, the second to fifth detection units 130 to 160 are arranged while the second to fifth detection units 130 to 160 avoid the region of an electric field spread by the first signal line 121 and the first GND line 122 of the first detection unit 120. The first GND line 122 and the second GND line 132 are arranged adjacent to each other. Similarly, the first GND line 122 and the third GND line 142 are arranged adjacent to each other. The second GND line 132 and the fourth GND line 152 are arranged adjacent to each other. The first GND line 122 and the fifth GND line 162 are arranged adjacent to each other. Unnecessary capacitance is thus not generated among the detection units 120 to 160. Mutual influence can be therefore reduced among the detection units 120 to 160.

The water potential indicates water absorbency of roots, and the electric conductivity indicates the salinity concentration of the soil 200. The soil sensor 100 can measure the water potential and the electric conductivity. The soil sensor 100 is thus suitable for feedback control regarding the components and amount of a liquid fertilizer for the soil 200.

The one surface 111 of the base 110 according to the present embodiment corresponds to an installation surface.

Second Embodiment

Figure 7:
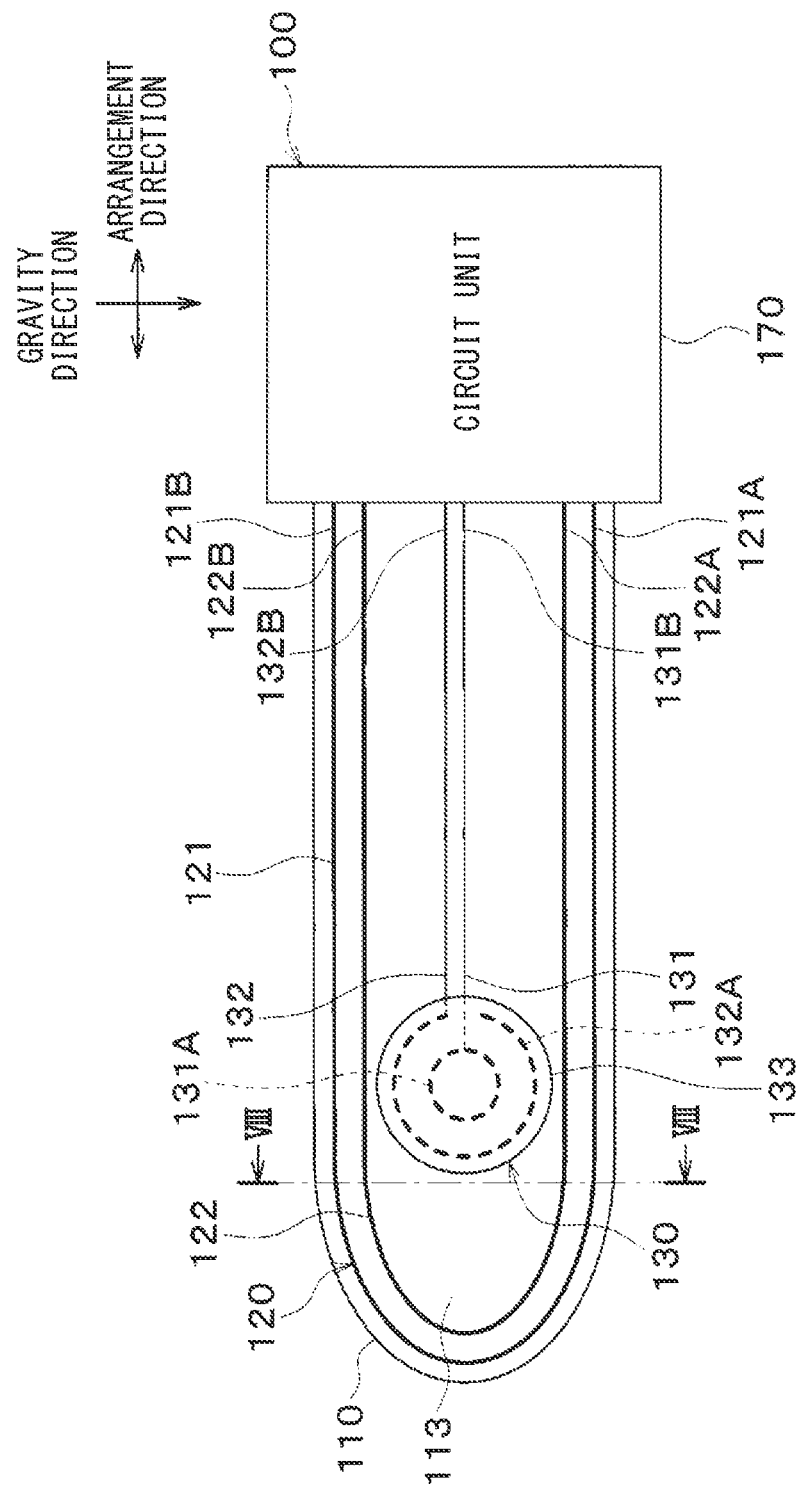
FIG. 7 is a plan view of a soil sensor according to a second embodiment.
Figure 8:
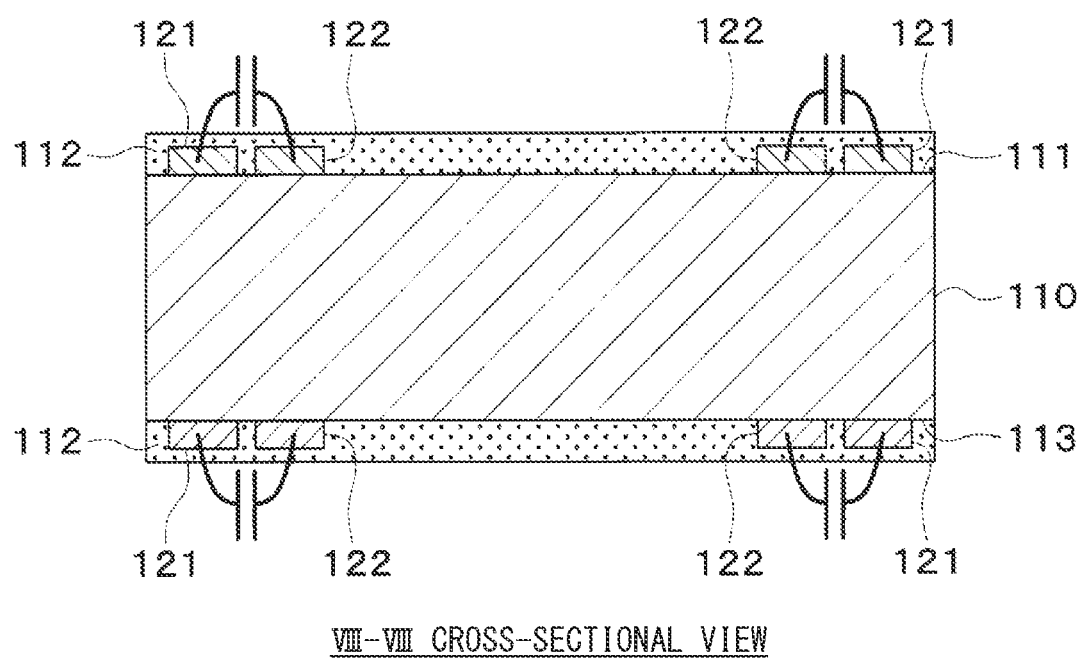
FIG. 8 is a cross-sectional view taken along line VIII-VIII of FIG. 7.

In the present embodiment, the description primarily focuses on the portions that differ from the first embodiment. As illustrated in FIGS. 7 and 8, the base 110 includes the other surface 113 opposite to the one surface 111. The first detection unit 120 is arranged on each side of the base 110, that is, both of the one surface 111 of the base 110 and the other surface 113 of the base 110. The first signal line 121 and the first GND line 122 arranged on the other surface 113 of the base 110 are also covered with another insulating film 112. The detection units 120 to 160 are also installed to the other surface 113 of the base 110 as well as to the one surface 111 of the base 110. In FIG. 8, the illustration of the second to fifth detection units 130 to 160 is omitted.

The above configuration enables an increase in the arrangement density of the wiring patterns of the first detection unit 120 and the second detection unit 130. That is, a longer wiring pattern can be formed in total within the ranges of the one surface 111 and the other surface 113 of the base 110. Thus, the sensitivity of the first detection unit 120 and the second detection unit 130 can be enhanced, and the soil sensor 100 can be downsized.

The first signal line 121 and the first GND line 122 of the first detection unit 120 are allowed to be close to each other, and thus the electric field easily permeates through the soil 200. The sensitivity can be therefore further enhanced.

The other surface 113 of the base 110 according to the present embodiment corresponds to the installation surface.

Third Embodiment

Figure 9:
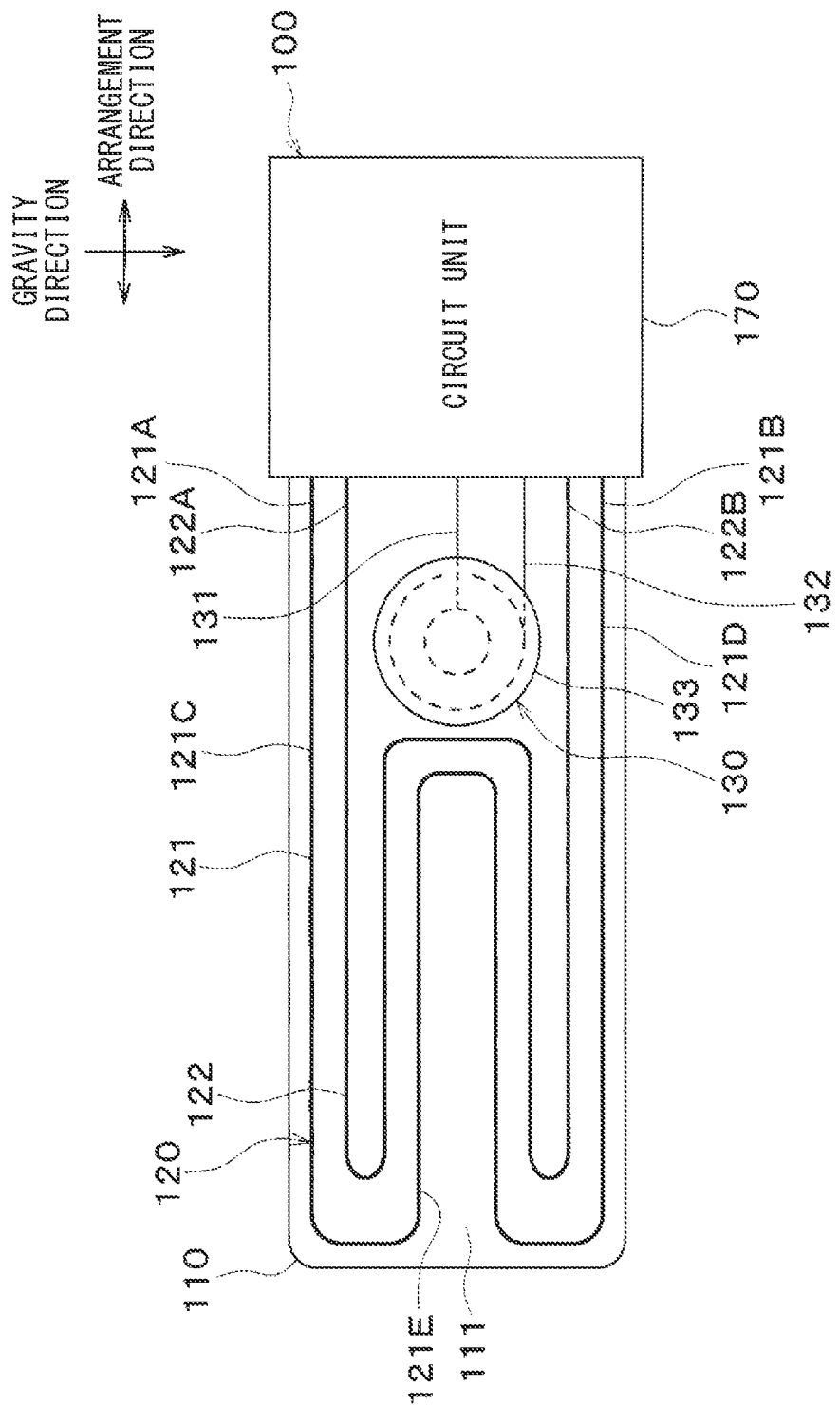
FIG. 9 is a plan view of a soil sensor according to a third embodiment.

In the present embodiment, the description primarily focuses on the portions that differ from the first and second embodiments. As illustrated in FIG. 9, the connection portion 121E of the first detection unit 120 is a wiring pattern folded toward the wiring pattern of the first straight portion 121C corresponding to the one end portion 121A of the first signal line 121 and the wiring pattern of the second straight portion 121D corresponding to the other end portion 121B of the first signal line 121. In FIG. 9, the illustration of the third to fifth detection units 140 to 160 is omitted.

The first GND line 122 is spaced from the first signal line 121 at the first interval. Thus, a portion of the first GND line 122 corresponding to the connection portion 121E is also a wiring pattern folded toward the one end portion 122A of the first GND line 122 and the other end portion 122B of the first GND line 122.

Figure 10:
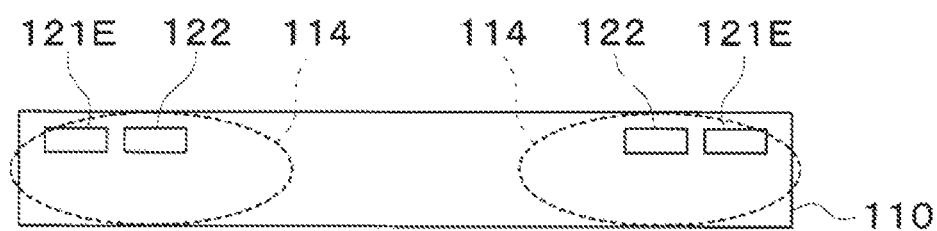
FIG. 10 is a schematic diagram illustrating a spreading manner of electric fields when the density of wiring patterns is low.

For example, the soil 200 having absorbed water has high permittivity. A difference in permittivity between the base 110 and the soil 200 thus increases. As illustrated in FIG. 10, the total reflection of each electric field 114 therefore occurs at the interface between the base 110 and the soil 200. That is, the electric field 114 does not pass through the soil 200, and thus the sensitivity to a change in permittivity of the soil 200 decreases.

Figure 11:
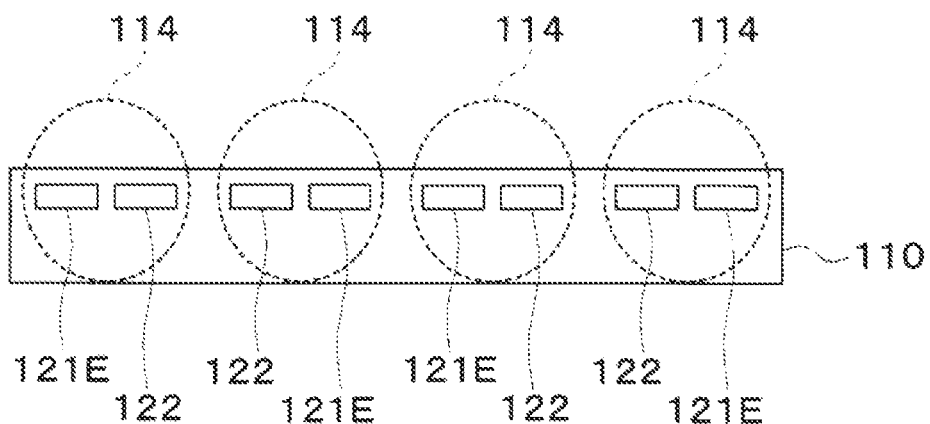
FIG. 11 is a schematic diagram illustrating a spreading manner of electric fields when the density of wiring patterns is high.

In contrast, when the connection portion 121E is the folded wiring pattern as described above, the density of the wiring pattern in which the connection portion 121E is folded is higher than the density of the wiring pattern in which the connection portion 121E is not folded. The angle of incidence of each electric field with respect to the interface between the base 110 and the soil 200 thus increases. The total reflection of each electric field 114 therefore does not occur at the interface between the base 110 and the soil 200, as illustrated in FIG. 11. The sensitivity of the first detection unit 120 can be therefore enhanced.

As a modification, the connection portion 121E may be folded not once but a plurality of times. In this case, the connection portion 121E is a meandering wiring pattern.

Fourth Embodiment

Figure 12:
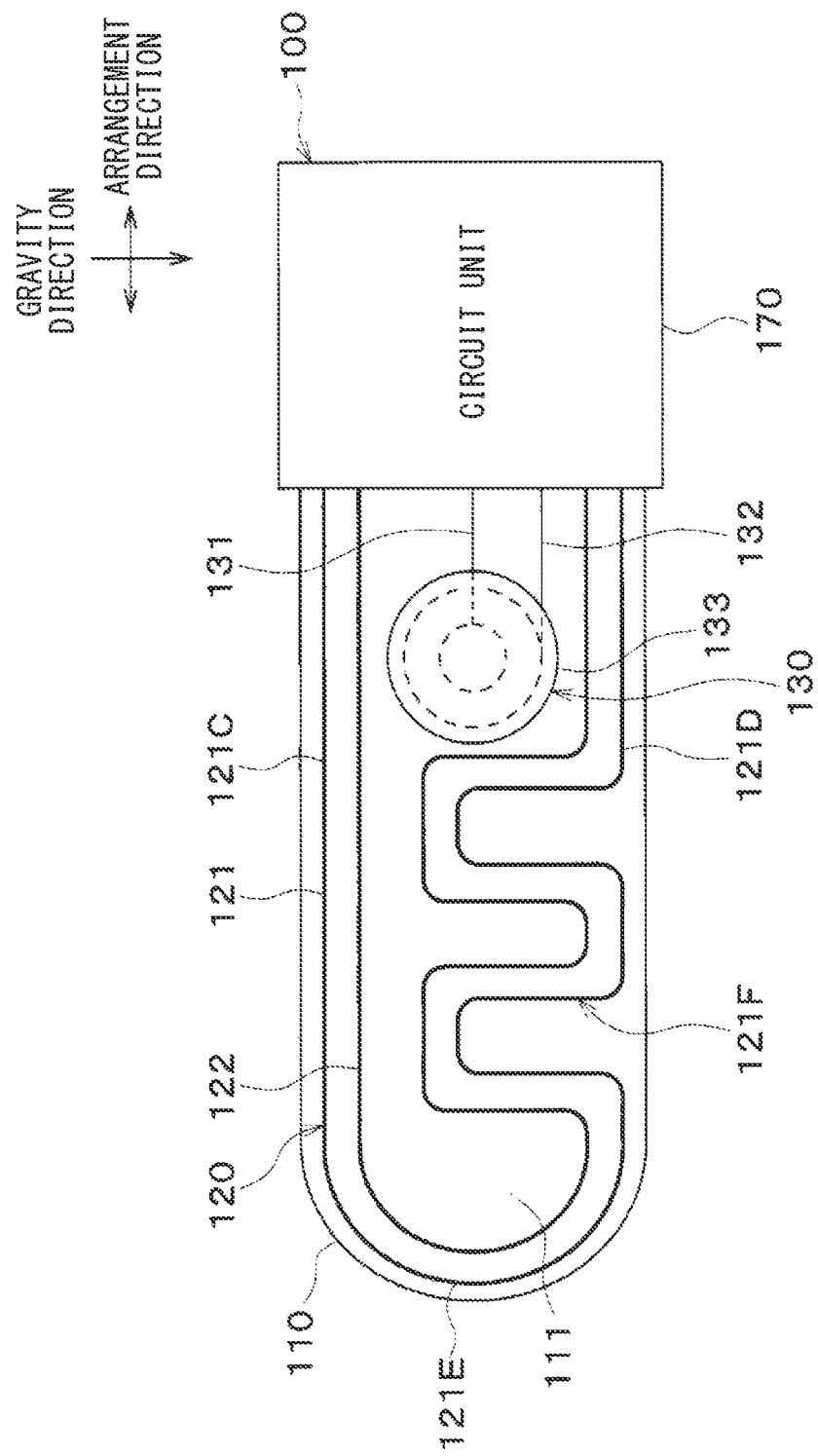
FIG. 12 is a plan view of a soil sensor according to a fourth embodiment.

In the present embodiment, the description primarily focuses on the portions that differ from the above embodiments. As illustrated in FIG. 12, the second straight portion 121D of the first signal line 121 includes a wiring pattern portion 121F having a meandering pattern. The meandering pattern is a wavelike pattern or a repeated pattern. In FIG. 12, the illustration of the third to fifth detection units 140 to 160 is omitted.

The first GND line 122 is a wiring pattern spaced from the first signal line 121 at the first interval. A portion of the first GND line 122 corresponding to the second straight portion 121D of the first signal line 121 is thus a meandering pattern. The above configuration enables an increase in the density of the wiring pattern of the first detection unit 120. An effect similar to that of the third embodiment can be thus obtained.

As a modification, the first straight portion 121C may include a meandering wiring pattern portion. That is, one of the first straight portion 121C and the second straight portion 121D includes a meandering pattern portion.

As another modification, one of the first straight portion 121C and the second straight portion 121D may include a meandering wiring pattern portion, and the connection portion 121E may include a folded wiring pattern.

Fifth Embodiment

Figure 13:
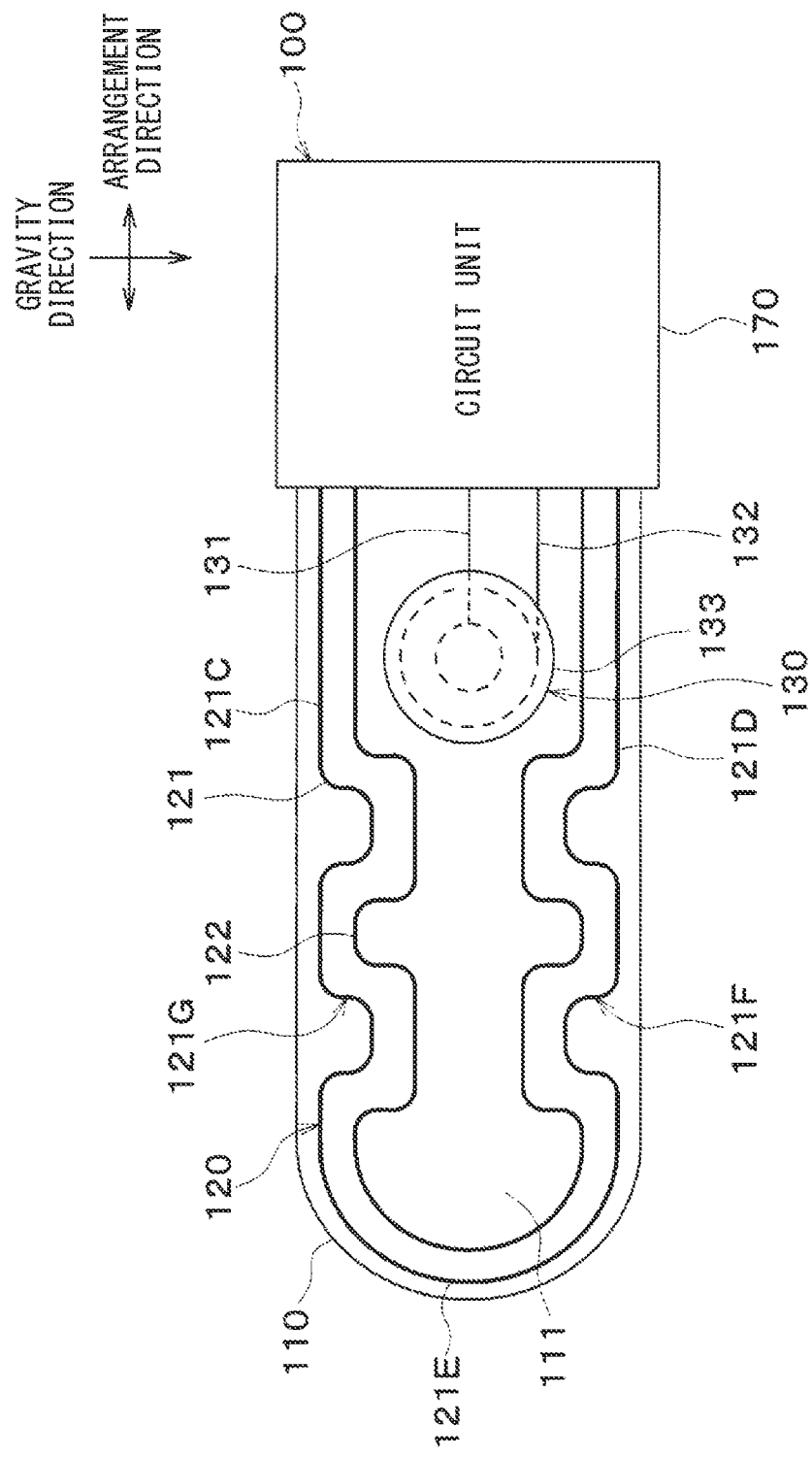
FIG. 13 is a plan view of a soil sensor according to a fifth embodiment.

In the present embodiment, the description primarily focuses on the portions that differ from the fourth embodiment. As illustrated in FIG. 13, the first straight portion 121C of the first signal line 121 includes a first wiring pattern portion 121G having a meandering pattern. The second straight portion 121D of the first signal line 121 includes a second wiring pattern portion 121F having a meandering pattern. In FIG. 13, the illustration of the third to fifth detection units 140 to 160 is omitted. In the first GND line 122, respective portions corresponding to the straight portions 121C, 121D of the first signal line 121 are respective meandering wiring patterns. According to the above configuration, an effect similar to that of the third embodiment can be obtained.

As a modification, both the first straight portion 121C and the second straight portion 121D may include respective meandering wiring pattern portions, and the connection portion 121E may include a folded wiring pattern.

Sixth Embodiment

Figure 14:
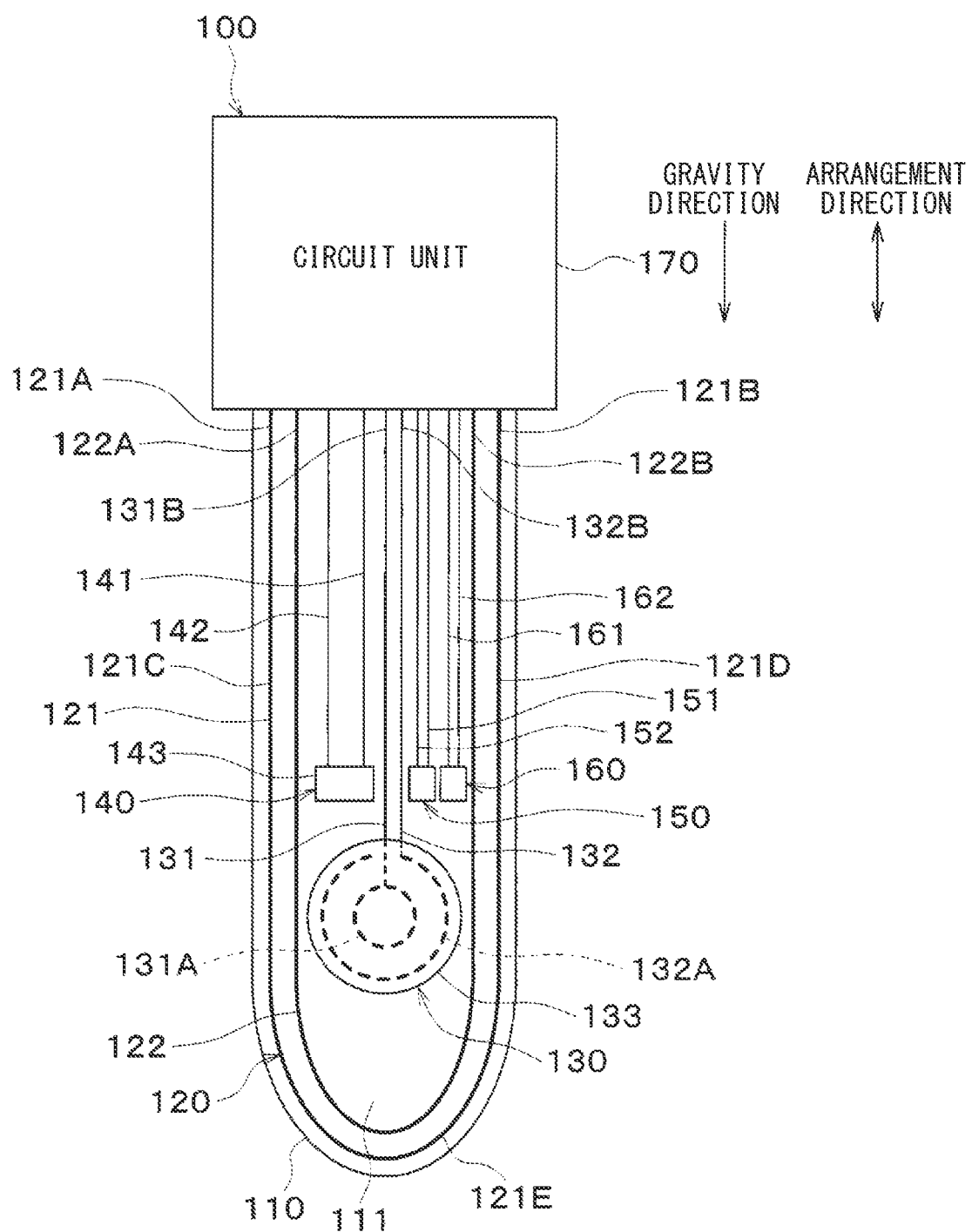
FIG. 14 is a plan view of a soil sensor according to a sixth embodiment.

In the present embodiment, the description primarily focuses on the portions that differ from the above embodiments. As illustrated in FIG. 14, the soil sensor 100 is arranged such that the circuit unit 170 is positioned on the upper side of the base 110 in the gravity direction. That is, the arrangement direction and the gravity direction are parallel to each other. The arrangement direction may be slightly inclined with respect to the gravity direction as well as being parallel to the gravity direction.

For example, when the soil 200 is culture soil, a fertilizer and water are mixed at a certain proportion. The culture soil is soil in which a fertilizer, and other components including leaf mold, sand, peat moss, vermiculite, and lime are mixed at a certain proportion to cultivate plants. Accordingly, the soil sensor 100 can be vertically arranged in the soil 200, as illustrated in FIG. 14.

Seventh Embodiment

Figure 15:
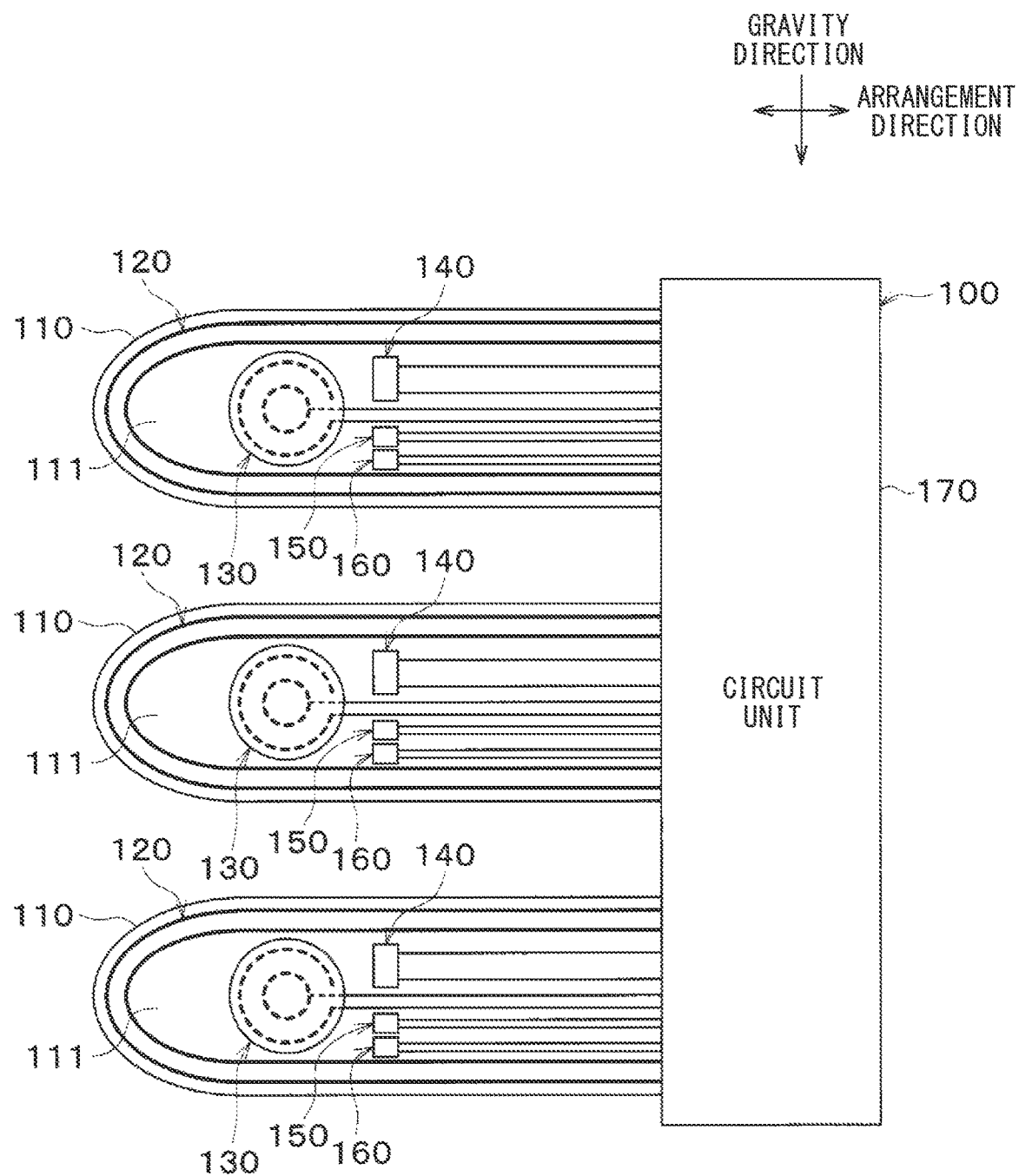
FIG. 15 is a plan view of a soil sensor according to a seventh embodiment.

In the present embodiment, the description primarily focuses on the portions that differ from the first embodiment. As illustrated in FIG. 15, the soil sensor 100 includes a plurality of first detection units 120, a plurality of second detection units 130, a plurality of third detection units 140, a plurality of fourth detection units 150, and a plurality of fifth detection units 160. Specifically, the soil sensor 100 includes a plurality of bases 110. The plurality of bases 110 is arranged in the gravity direction to obtain physical quantities such as water contents, electric conductivity, and water potentials at different positions in the gravity direction. Each set of the detection units 120 to 160 is installed in a corresponding one of respective one surfaces 111 of the bases 110.

The soil sensor 100 is arranged in the soil 200 such that the arrangement direction is oriented in a direction perpendicular to the gravity direction. As a result, physical quantities can be measured for each level in the depth direction of the soil 200. The soil sensor 100 may be arranged in the soil 200 such that the arrangement direction is along the gravity direction.

Figure 16:
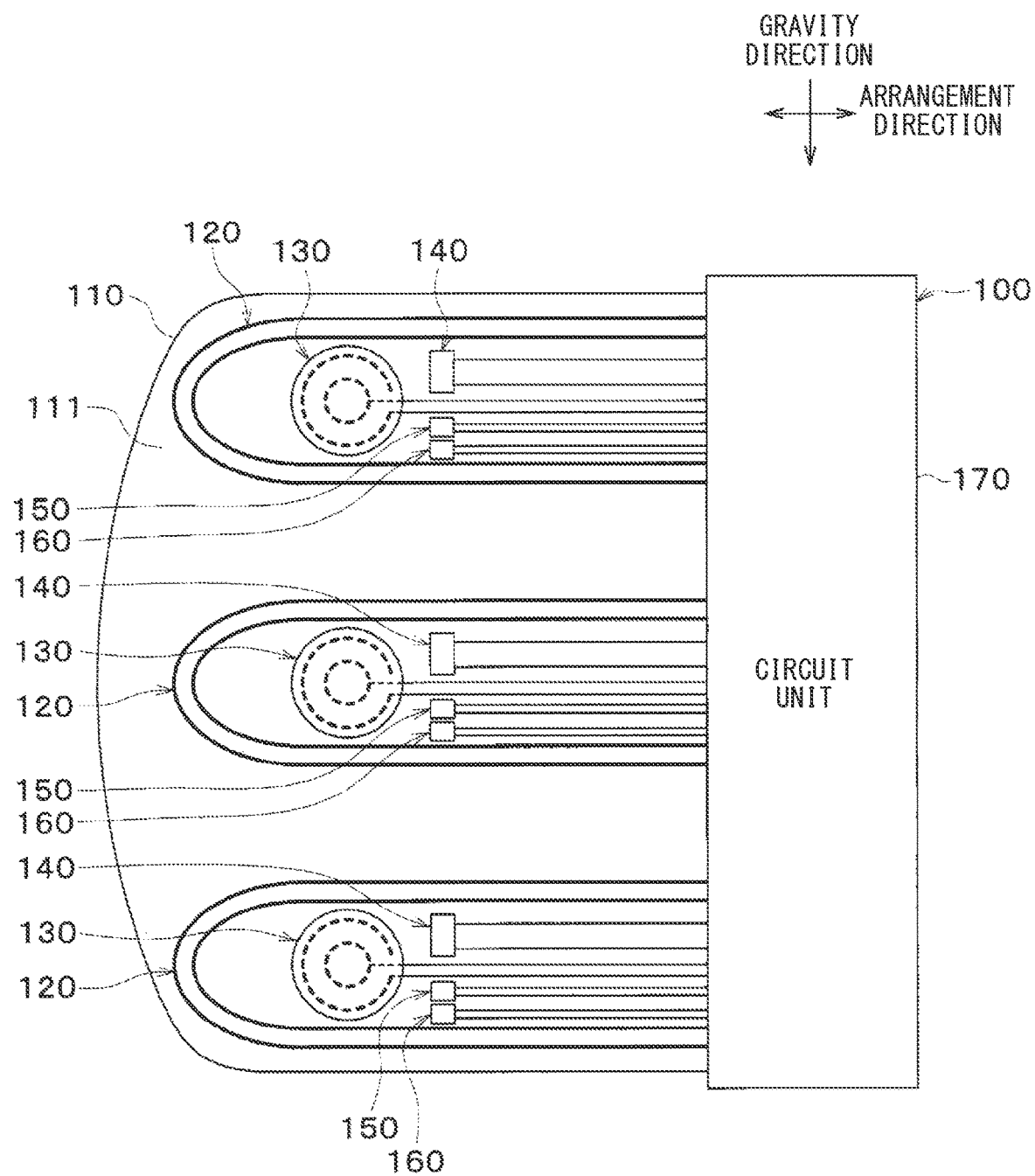
FIG. 16 is a plan view illustrating a modification of the soil sensor according to the seventh embodiment.

As a modification, a single base 110 may be provided, and each set of the detection units 120 to 160 may be installed to one surface 111 of the single base 110, as illustrated in FIG. 16.

As another modification, all the detection units 120 to 160 may not be arranged at different positions in the gravity direction. That is, one or some of the detection units 120 to 160 may be arranged at different positions in the gravity direction. For example, only the first detection unit 120 may be arranged at a different position in the gravity direction, or only the second detection unit 130 may be arranged at a different position in the gravity direction.

Eighth Embodiment

Figure 17:
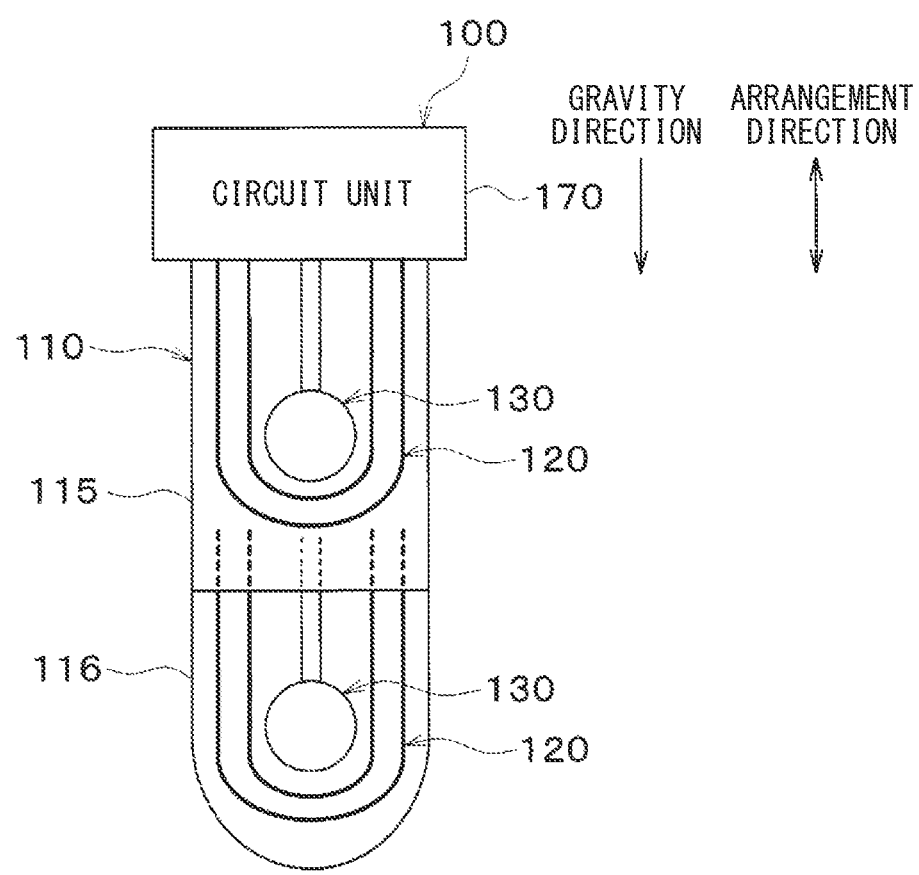
FIG. 17 is a plan view of a soil sensor according to an eighth embodiment.
Figure 18:
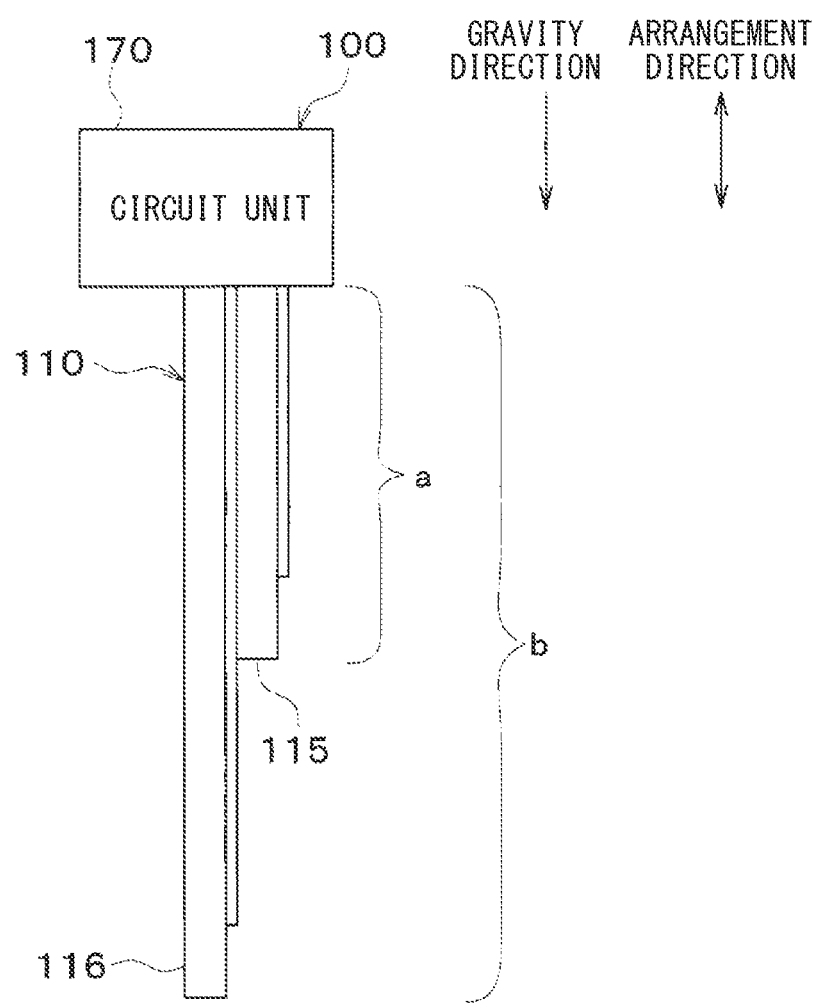
FIG. 18 is a side view of the soil sensor illustrated in FIG. 17.

In the present embodiment, the description primarily focuses on the portions that differ from the seventh embodiment. As illustrated in FIGS. 17 and 18, the soil sensor 100 is configured such that the circuit unit 170 is arranged on the upper side in the gravity direction, in the present embodiment. In FIG. 17, the illustration of the third to fifth detection units 140 to 160 is omitted.

The base 110 includes a first base 115 and a second base 116 that have different lengths in the arrangement direction. The first base 115 has a length "a" in the arrangement direction. The second base 116 has a length "b" in the arrangement direction, which is longer than the length "a". A part of the second base 116 on one end side thereof is exposed, by overlapping and integrating the first base 115 with the second base 116.

The above configuration enables measurement of each physical quantity at a depth corresponding to the tip portion of the second base 116, that is, the portion of the second base 116 having a range obtained by subtracting "a" from "b".

The soil sensor 100 may be arranged in the soil 200 such that the arrangement direction is oriented in the direction perpendicular to the gravity direction.

Figure 19:
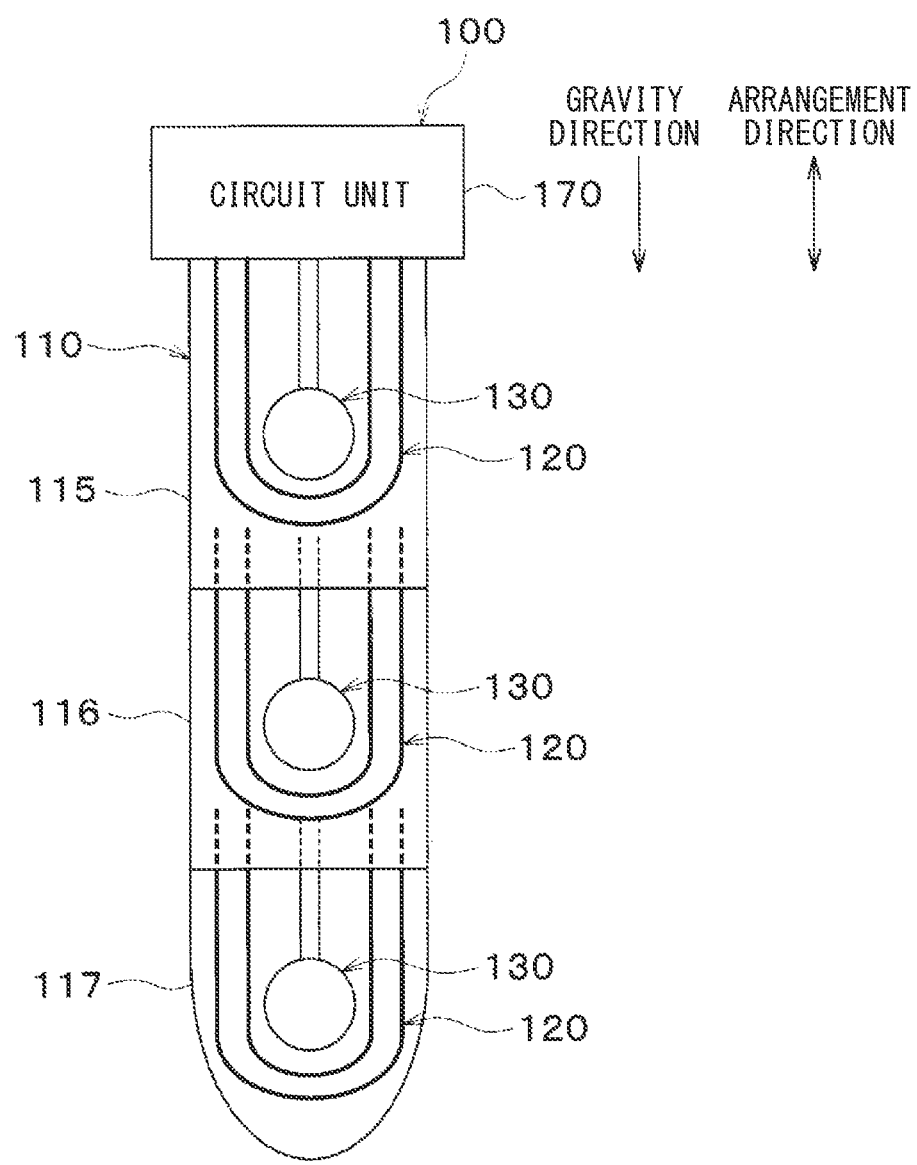
FIG. 19 is a plan view illustrating a modification of the soil sensor according to the eighth embodiment.
Figure 20:
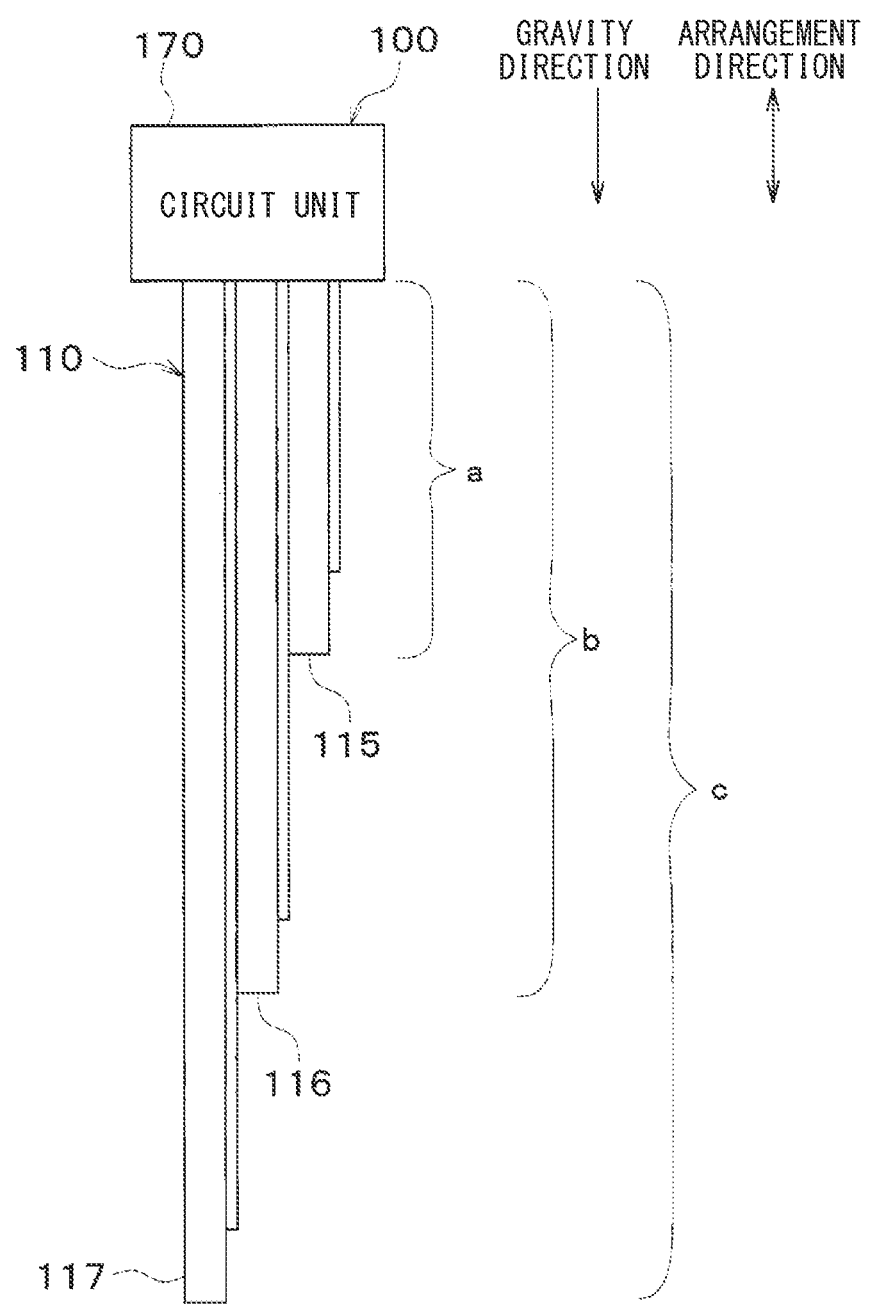
FIG. 20 is a side view of the soil sensor illustrated in FIG. 19.

As a modification, the base 110 may further include a third base 117 that has a length c in the arrangement direction longer than the length b, as illustrated in FIGS. 19 and 20. The second base 116 is overlapped and integrated with the third base 117. This configuration enables measurement of each physical quantity at a depth corresponding to the tip portion of the third base 117, that is, the portion of the third base 117 having a range obtained by subtracting b from c, as well as the depth corresponding to the tip portion of the second base 116.

Figure 21:
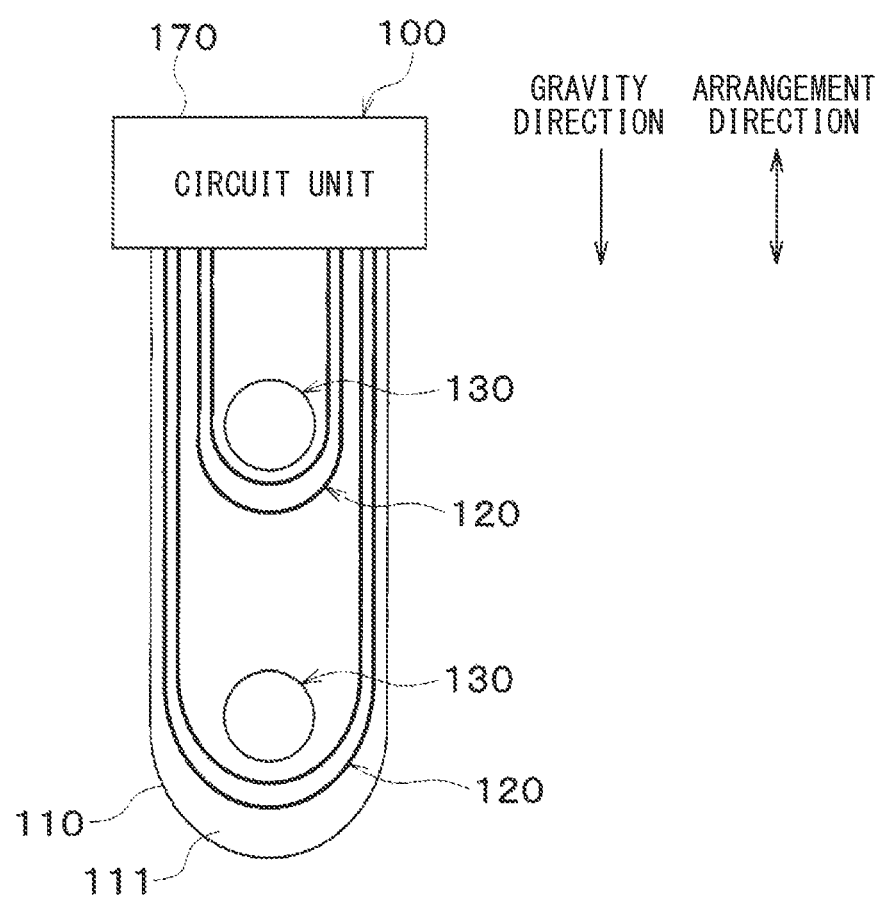
FIG. 21 is a plan view illustrating another modification of the soil sensor according to the eighth embodiment.
Figure 22:
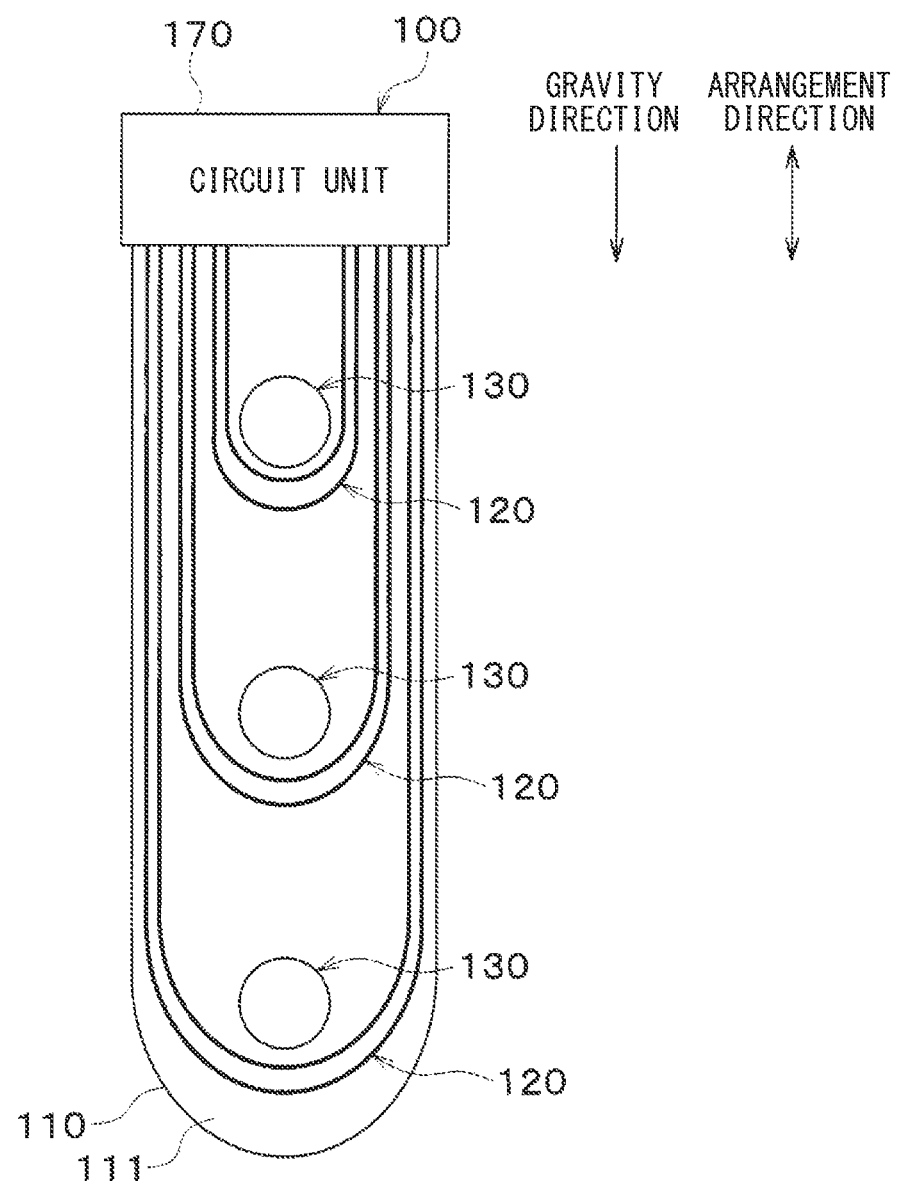
FIG. 22 is a plan view illustrating still another modification of the soil sensor according to the eighth embodiment.

As another modification, the base 110 may be a single base, as illustrated in FIG. 21. Each set of the detection units 120 to 160 is arranged in two stages in the arrangement direction in the one surface 111 of the base 110. Alternatively, each set of the detection units 120 to 160 may be arranged in three stages in the arrangement direction in the one surface 111 of the base 110, as illustrated in FIG. 22. In FIGS. 21 and 22, the illustration of the third to fifth detection units 140 to 160 is omitted.

Ninth Embodiment

Figure 23:
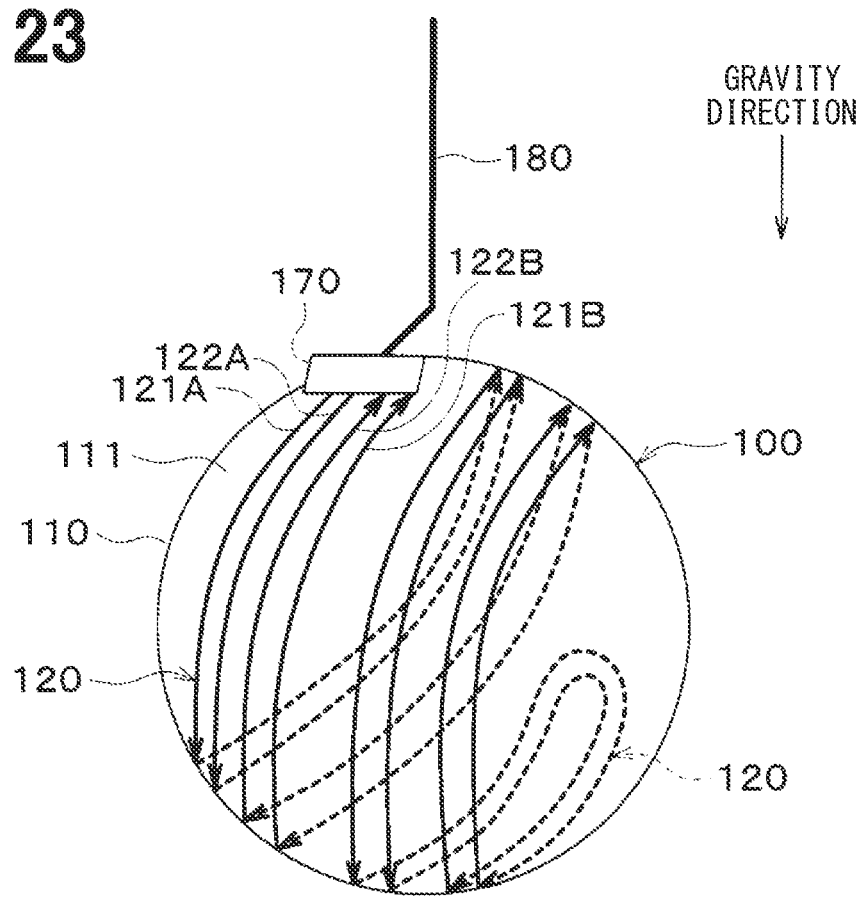
FIG. 23 is a perspective view of a soil sensor according to a ninth embodiment.

In the present embodiment, the description primarily focuses on the portions that differ from the above embodiments. As illustrated in FIG. 23, the base 110 is not formed as a board or a substrate, but is formed as a sphere. The surface of the sphere corresponds to the one surface 111. The sphere is, for example, a resin ball.

Each of the detection units 120 to 160 is arranged to the surface of the sphere. The wiring pattern of each of the detection units 120 to 160 is printed on the surface of the sphere, for example. In FIG. 23, the illustration of the second to fifth detection units 130 to 160 is omitted.

The above configuration allows the wiring patterns of the first detection unit 120 to be formed on the sphere in a repeatedly circling manner. The wiring patterns of the first detection unit 120 can be thus lengthened. The sensitivity of the first detection unit 120 can be therefore enhanced.

As a modification, the base 110 may have a slightly deformed shape such as an ellipsoid, instead of being formed as a complete sphere.

Tenth Embodiment

Figure 24:
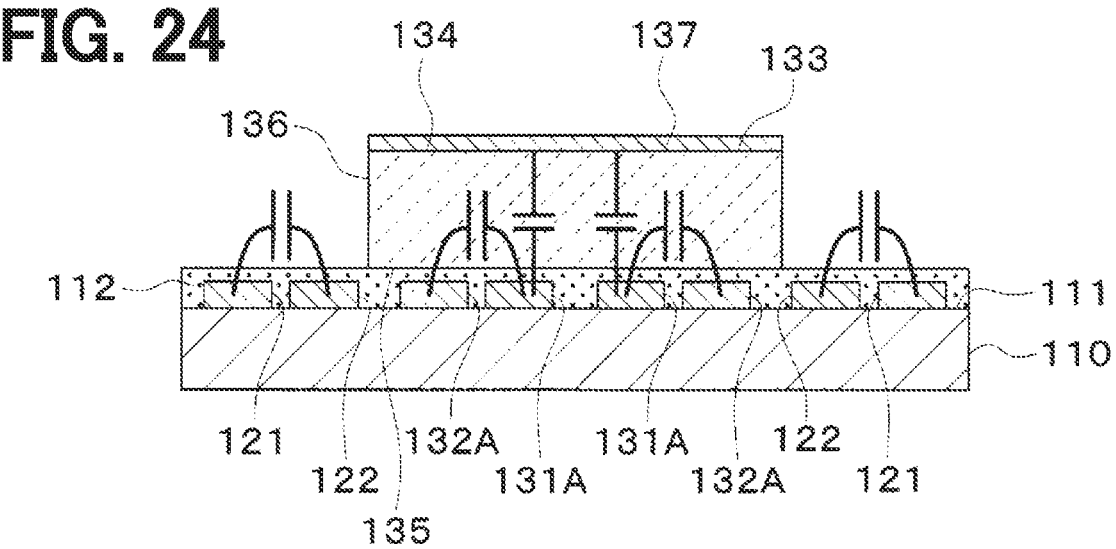
FIG. 24 is a cross-sectional view of a soil sensor according to a tenth embodiment.

In the present embodiment, the description primarily focuses on the portions that differ from the above embodiments. As illustrated in FIG. 24, the ceramic body 133 includes an obverse surface 134, a reverse surface 135, and a side surface 136. The ceramic body 133 is arranged such that the reverse surface 135 is positioned on the side of the one end portion 131A of the second signal line 131 and the one end portion 132A of the second GND line 132. That is, the reverse surface 135 of the ceramic body 133 is contact with the insulating film 112. In FIG. 24, the illustration of the third to fifth detection units 140 to 160 is omitted.

The second detection unit 130 includes a metal body 137. The metal body 137 is arranged on the entire area of the obverse surface 134 of the ceramic body 133. The metal body 137 is formed of, for example, a metal material having excellent corrosion resistance such as aluminum or stainless steel. The metal body 137 may include a single layer or a plurality of layers. When the metal body 137 includes a plurality of layers, the plurality of layers may be formed of the same metal material, or the plurality of layers may be formed of different metal materials.

The metal body 137 is connected to a part of the second GND line 132 (not illustrated) arranged on the side surface 136 of the ceramic body 133. The metal body 137 is thus electrically connected to the second GND line 132. The metal body 137 is the other electrode with respect to the ceramic body 133.

The above configuration allows capacitance to be also generated between the one end portion 131A of the second signal line 131 positioned on the one surface 111 of the base 110 and the metal body 137. When capacitance necessary for measuring the water potential is denoted by C, an area is denoted by S, and a distance between the electrodes is denoted by d, the capacitance C is expressed as $C=\varepsilon \times (S/d)$. Accordingly, obtainable capacitance increases because the area of the electrode increases by the area of the metal body 137. The sensitivity of the second detection unit 130 can be therefore enhanced.

As a modification, the metal body 137 may be arranged on at least a part of the obverse surface 134 of the ceramic body 133.

Eleventh Embodiment

Figure 25:
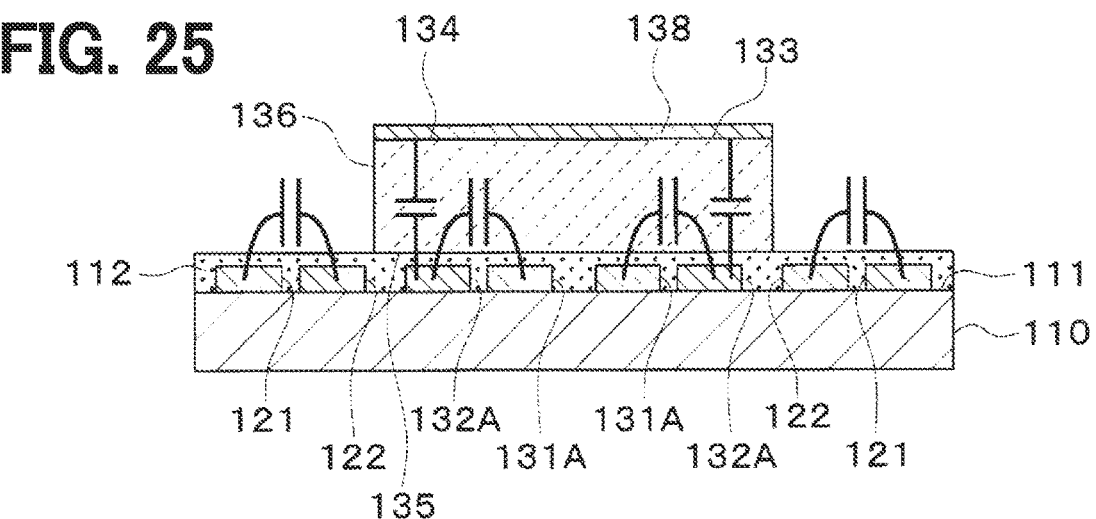
FIG. 25 is a cross-sectional view of a soil sensor according to an eleventh embodiment.

In the present embodiment, the description primarily focuses on the portions that differ from the tenth embodiment. As illustrated in FIG. 25, the second detection unit 130 includes a metal body 138. The metal body 138 is arranged on the entire area of the obverse surface 134 of the ceramic body 133. In FIG. 25, the illustration of the third to fifth detection units 140 to 160 is omitted.

The metal body 138 is connected to a part of the second signal line 131 (not illustrated) arranged on the side surface 136 of the ceramic body 133. The metal body 138 is thus electrically connected to the second signal line 131. The metal body 138 is the one electrode with respect to the ceramic body 133.

According to the above configuration, obtainable capacitance increases because the area of the electrode increases by the area of the metal body 138, similarly to the tenth embodiment. The sensitivity of the second detection unit 130 can be therefore enhanced.

As a modification, the metal body 138 may be arranged on at least a part of the obverse surface 134 of the ceramic body 133.

Twelfth Embodiment

Figure 26:
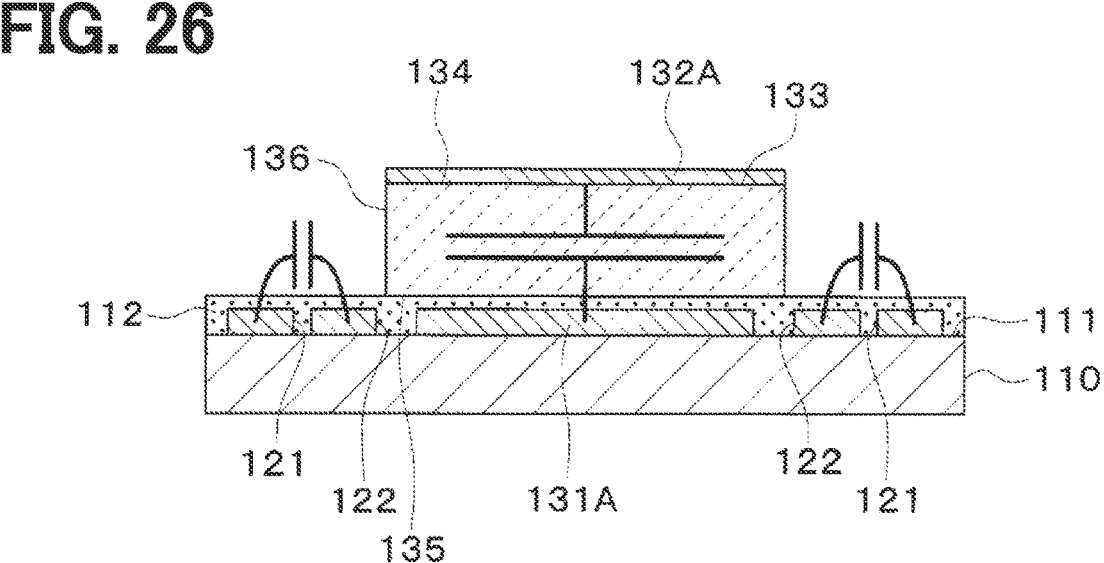
FIG. 26 is a cross-sectional view of a soil sensor according to a twelfth embodiment.

In the present embodiment, the description primarily focuses on the portions that differ from the above embodiments. As illustrated in FIG. 26, the one end portion 131A of the second signal line 131 is arranged on the one surface 111 of the base 110. The one end portion 131A of the second signal line 131 has, for example, a circular planar shape. In FIG. 26, the illustration of the third to fifth detection units 140 to 160 is omitted.

The ceramic body 133 is arranged such that the reverse surface 135 is positioned above the one end portion 131A of the second signal line 131. That is, the ceramic body 133 is arranged such that the reverse surface 135 is positioned on the side of the one end portion 131A of the second signal line 131.

The one end portion 132A of the second GND line 132 is arranged on the entire area of the obverse surface 134 of the ceramic body 133. The one end portion 132A of the second GND line 132 is electrically connected to a part of the second GND line 132 arranged on the side surface 136 of the ceramic body 133.

According to the above configuration, the area of the electrode formed by the one end portion 131A of the second signal line 131 and the one end portion 132A of the second GND line 132 becomes larger than that in the case of the first embodiment, and thus obtainable capacitance increases. The sensitivity of the second detection unit 130 can be therefore enhanced.

As a modification, the planar shape of the one end portion 131A of the second signal line 131 may be an elliptical shape or a polygonal shape. The one end portion 132A of the second GND line 132 may be arranged on at least a part of the obverse surface 134 of the ceramic body 133.

As another modification, the second GND line 132 may be connected to the first GND line 122 of the first detection unit 120. This configuration allows the second GND line 132 to be shared through the first GND line 122.

Thirteenth Embodiment

Figure 27:
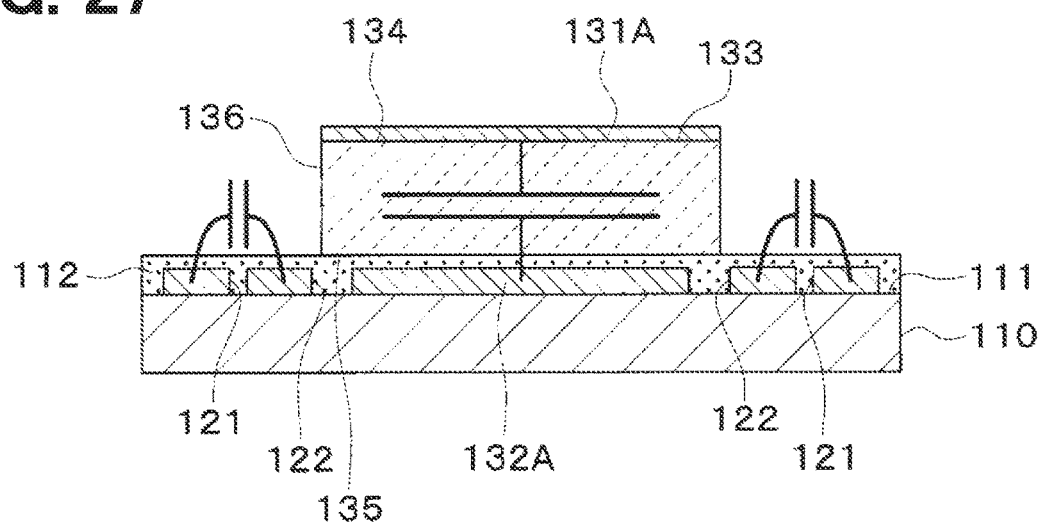
FIG. 27 is a cross-sectional view of a soil sensor according to a thirteenth embodiment.

In the present embodiment, the description primarily focuses on the portions that differ from the twelfth embodiment. As illustrated in FIG. 27, the one end portion 132A of the second GND line 132 is arranged on the one surface 111 of the base 110. The one end portion 132A of the second GND line 132 has, for example, a circular planar shape. In FIG. 27, the illustration of the third to fifth detection units 140 to 160 is omitted.

The ceramic body 133 is arranged such that the reverse surface 135 is positioned above the one end portion 132A of the second GND line 132. That is, the ceramic body 133 is arranged such that the reverse surface 135 is positioned on the side of the one end portion 132A of the second GND line 132.

The one end portion 131A of the second signal line 131 is arranged on the entire area of the obverse surface 134 of the ceramic body 133. The one end portion 131A of the second signal line 131 is electrically connected to a part of the second signal line 131 arranged on the side surface 136 of the ceramic body 133.

According to the above configuration, obtainable capacitance increases, similarly to the twelfth embodiment. The sensitivity of the second detection unit 130 can be therefore enhanced.

As a modification, the planar shape of the one end portion 132A of the second GND line 132 may be an elliptical shape or a polygonal shape. The one end portion 131A of the second signal line 131 may be arranged on at least a part of the obverse surface 134 of the ceramic body 133.

Fourteenth Embodiment

Figure 28:
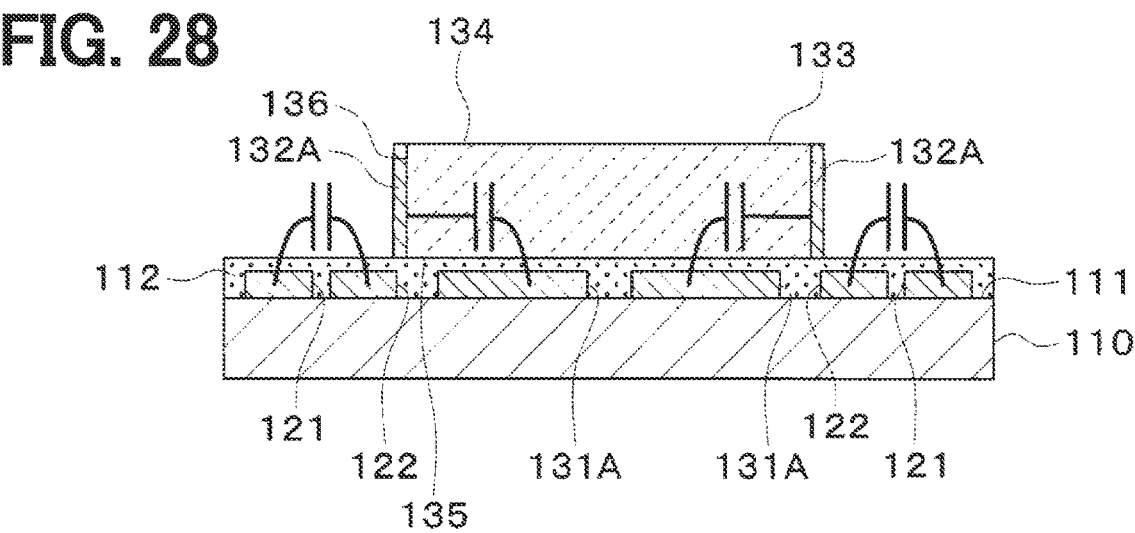
FIG. 28 is a cross-sectional view of a soil sensor according to a fourteenth embodiment.

In the present embodiment, the description primarily focuses on the portions that differ from the twelfth embodiment. The one end portion 131A of the second signal line 131 has, for example, an annular planar shape. As illustrated in FIG. 28, the one end portion 132A of the second GND line 132 is arranged on the entire area of the side surface 136 of the ceramic body 133. In FIG. 28, the illustration of the third to fifth detection units 140 to 160 is omitted.

The above configuration allows capacitance to be generated between the one end portion 132A of the second GND line 132 positioned on the side surface 136 of the ceramic body 133 and the one end portion 131A of the second signal line 131 positioned on the one surface 111 of the base 110. The one end portion 132A of the second GND line 132 is arranged on the entire area of the side surface 136 of the ceramic body 133, and thus obtainable capacitance increases. The sensitivity of the second detection unit 130 can be therefore enhanced.

As a modification, the planar shape of the one end portion 131A of the second signal line 131 may be an elliptical annular shape or a polygonal annular shape. The one end portion 132A of the second GND line 132 may be arranged on at least a part of the side surface 136 of the ceramic body 133.

Fifteenth Embodiment

Figure 29:
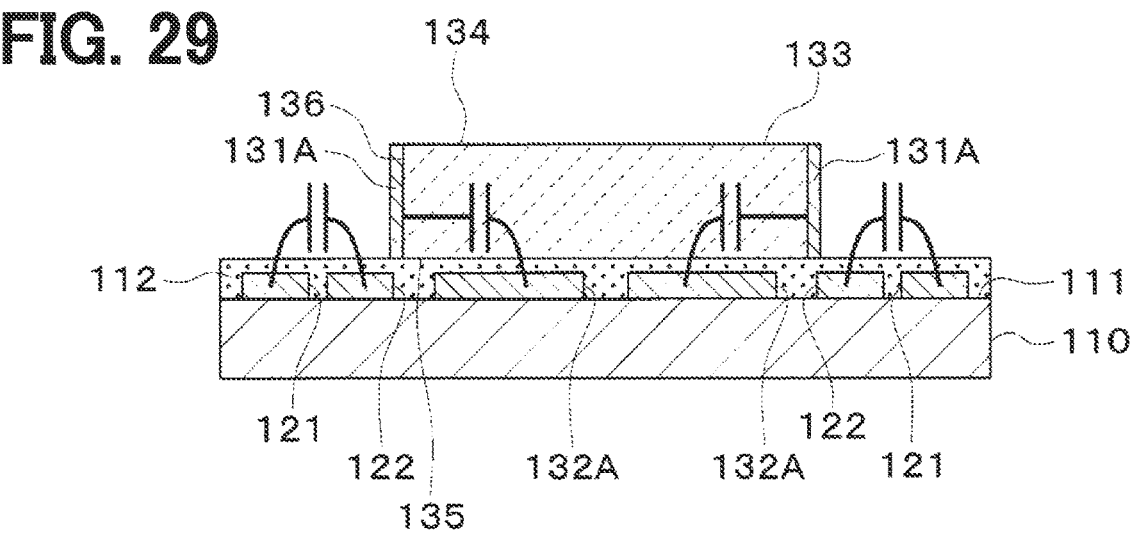
FIG. 29 is a cross-sectional view of a soil sensor according to a fifteenth embodiment.

In the present embodiment, the description primarily focuses on the portions that differ from the thirteenth embodiment. The one end portion 132A of the second GND line 132 has, for example, an annular planar shape. As illustrated in FIG. 29, the one end portion 131A of the second signal line 131 is arranged on the entire area of the side surface 136 of the ceramic body 133. In FIG. 29, the illustration of the third to fifth detection units 140 to 160 is omitted.

According to the above configuration, obtainable capacitance increases, similarly to the fourteenth embodiment. The sensitivity of the second detection unit 130 can be therefore enhanced.

As a modification, the planar shape of the one end portion 132A of the second GND line 132 may be an elliptical annular shape or a polygonal annular shape. The one end portion 131A of the second signal line 131 may be arranged on at least a part of the side surface 136 of the ceramic body 133.

Sixteenth Embodiment

Figure 30:
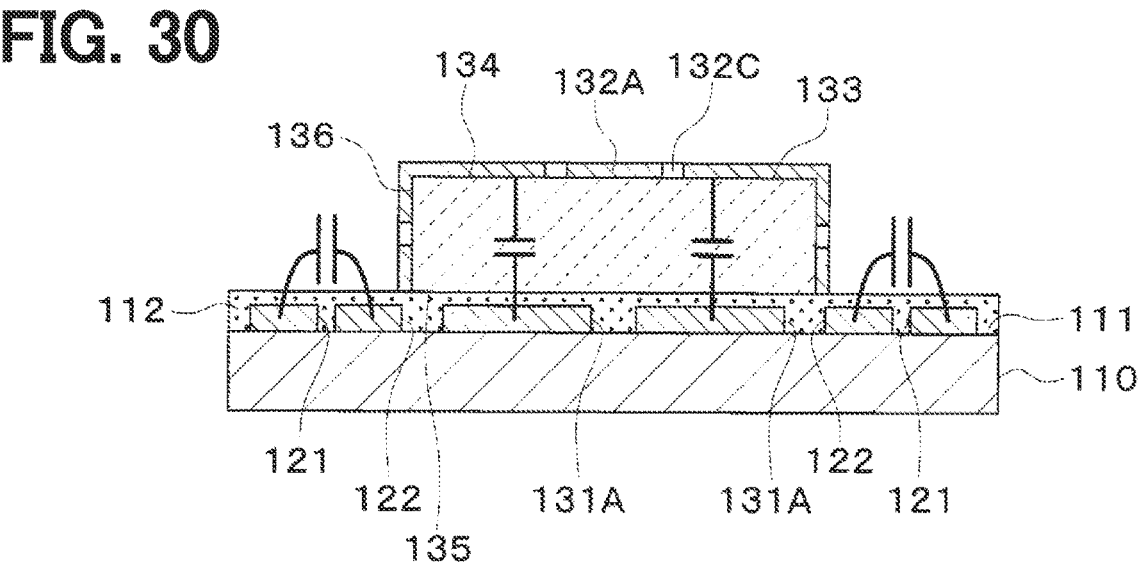
FIG. 30 is a cross-sectional view of a soil sensor according to a sixteenth embodiment.

In the present embodiment, the description primarily focuses on the portions that differ from the fourteenth embodiment. As illustrated in FIG. 30, the one end portion 132A of the second GND line 132 is arranged on the obverse surface 134 and the side surface 136 of the ceramic body 133. The one end portion 132A of the second GND line 132 includes a through hole 132C through which the ceramic body 133 is impregnated with the moisture of the soil 200. In FIG. 30, the illustration of the third to fifth detection units 140 to 160 is omitted.

According to the above configuration, obtainable capacitance increases, similarly to the fourteenth embodiment. The sensitivity of the second detection unit 130 can be therefore enhanced.

Seventeenth Embodiment

Figure 31:
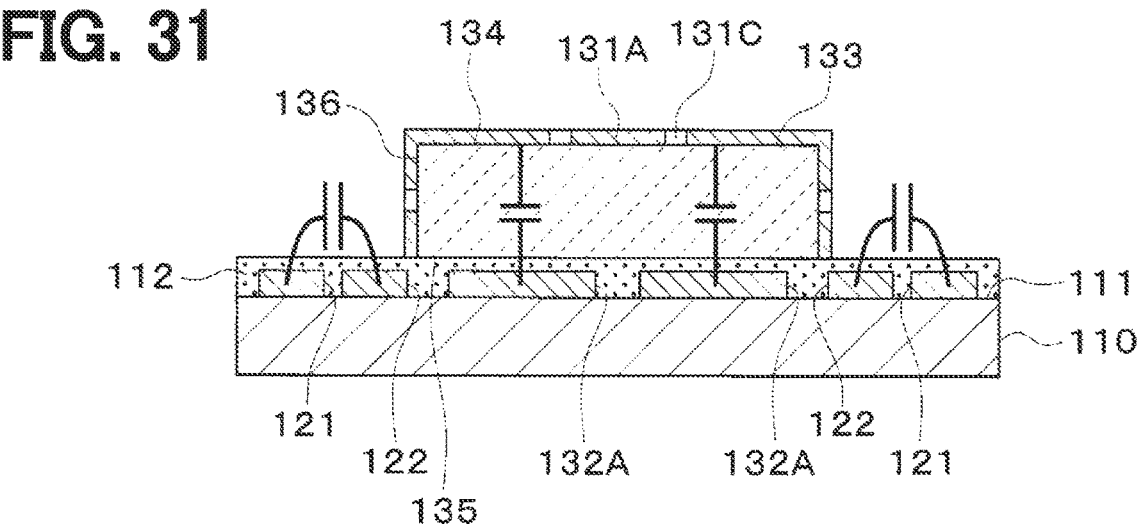
FIG. 31 is a cross-sectional view of a soil sensor according to a seventeenth embodiment.

In the present embodiment, the description primarily focuses on the portions that differ from the fifteenth embodiment. As illustrated in FIG. 31, the one end portion 131A of the second signal line 131 is arranged on the obverse surface 134 and the side surface 136 of the ceramic body 133. The one end portion 131A of the second signal line 131 includes a through hole 131C through which the ceramic body 133 is impregnated with the moisture of the soil 200. In FIG. 31, the illustration of the third to fifth detection units 140 to 160 is omitted.

According to the above configuration, obtainable capacitance increases, similarly to the fifteenth embodiment. The sensitivity of the second detection unit 130 can be therefore enhanced.

Eighteenth Embodiment

Figure 32:
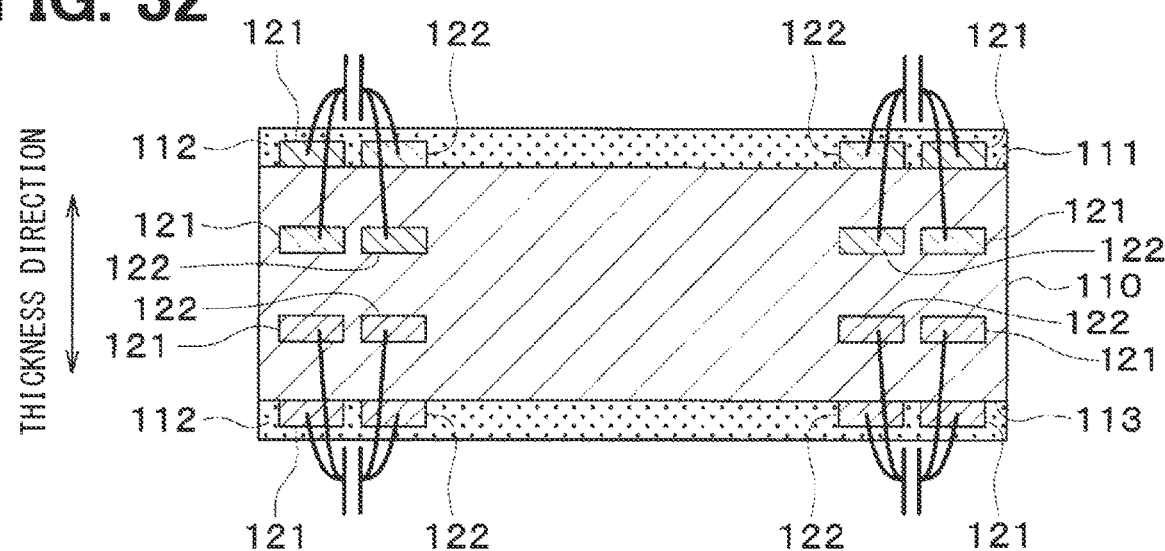
FIG. 32 is a cross-sectional view of a soil sensor according to an eighteenth embodiment.

In the present embodiment, the description primarily focuses on the portions that differ from the above embodiments. As illustrated in FIG. 32, installation of the first signal line 121 and the first GND line 122 is also made inside the base 110, in addition to the installation on each of the one surface 111 and the other surface 113 of the base 110. In FIG. 32, the illustration of the second to fifth detection units 130 to 160 is omitted.

The first signal line 121 includes a plurality of branched patterns branched in a plural manner between the one end portion 121A and the other end portion 121B. For example, the first signal line 121 includes four branched patterns connected in parallel between the one end portion 121A and the other end portion 121B. The four branched patterns extend along the one surface 111 of the base 110, and are in different positions in a thickness direction defined with respect to the one surface 111 of the base 110. The four branched patterns are thus layer-like wiring patterns. That is, the first signal line 121 includes four-level wiring patterns.

Similarly, the first GND line 122 also includes four branched patterns that extend along the one surface 111 of the base 110, and that are in different positions in the thickness direction defined with respect to the one surface 111 of the base 110. Each of the branched patterns of the first GND line 122 and a corresponding one of the branched patterns of the first signal line 121 are arranged at the same level.

The base 110 is, for example, a multi-layer substrate. With this configuration, the branched patterns of the first signal line 121 and the branched patterns of the first GND line 122 are decentralized in the thickness direction through vias formed in the multi-layer substrate. Each of the branched patterns of the first signal line 121 is converged into the one end portion 121A and the other end portion 121B. Similarly, each of the branched patterns of the first GND line 122 is converged into the one end portion 122A and the other end portion 122B.

According to the above configuration, electric field intensity increases by a degree corresponding to the additional provision of the branched patterns of the first signal line 121 and the branched patterns of the first GND line 122. The sensitivity of the first detection unit 120 can be therefore enhanced.

As a modification, the first signal line 121 and the first GND line 122 may not be arranged on the side of the other surface 113 of the base 110. That is, an arrangement of the first signal line 121 and the first GND line 122 may be made on the one surface 111 of the base 110 and inside the base 110.

As another modification, the number of levels at which the respective branched patterns of the first signal line 121 and the respective branched patterns of the first GND line 122 are positioned is not limited to four, and may be three or more. For example, the number of levels for the branched patterns of the first signal line 121 and the branched patterns of the first GND line 122 can be any of 6, 8, 10, and 12.

Nineteenth Embodiment

Figure 33:
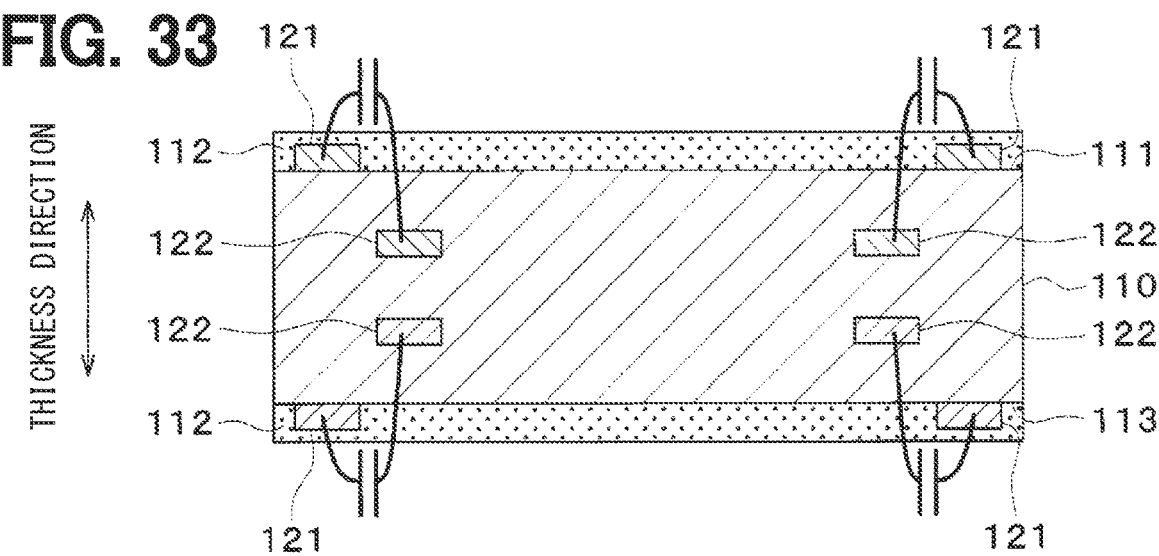
FIG. 33 is a cross-sectional view of a soil sensor according to a nineteenth embodiment.

In the present embodiment, the description primarily focuses on the portions that differ from the eighteenth embodiment. As illustrated in FIG. 33, an arrangement of the first signal line 121 and an arrangement of the first GND line 122 are made at different depths defined with respect to the one surface 111 of the base 110, in a thickness direction perpendicular to the one surface 111 of the base 110. In the present embodiment, the first signal line 121 is arranged on each of the one surface 111 and the other surface 113 of the base 110. In contrast, an arrangement of the first GND line 122 is made inside the base 110. In FIG. 33, the illustration of the second to fifth detection units 130 to 160 is omitted.

According to the above configuration, electric field intensity can be increased in the thickness direction of the base 110. The sensitivity of the first detection unit 120 can be therefore enhanced.

As a modification, an arrangement of the first signal line 121 may be made inside the base 110, while an arrangement of the first GND line 122 may be made on each of the one surface 111 and the other surface 113 of the base 110.

As another modification, an arrangement of the first signal line 121 may be made inside the base 110, an arrangement of the first GND line 122 may be made on the one surface 111 of the base 110, another arrangement of the first signal line 121 may be made on the other surface 113 of the base 110, and another arrangement of the first GND line 122 may be made inside the base 110.

As still another modification, an arrangement of the first signal line 121 may be made on the one surface 111 of the base 110, an arrangement of the first GND line 122 may be made inside the base 110, another arrangement of the first signal line 121 may be made inside the base 110, and another arrangement of the first GND line 122 may be made on the other surface 113 of the base 110.

As yet another modification, an arrangement of the first signal line 121 and the first GND line 122 may be made entirely inside the base 110.

Twentieth Embodiment

Figure 34:
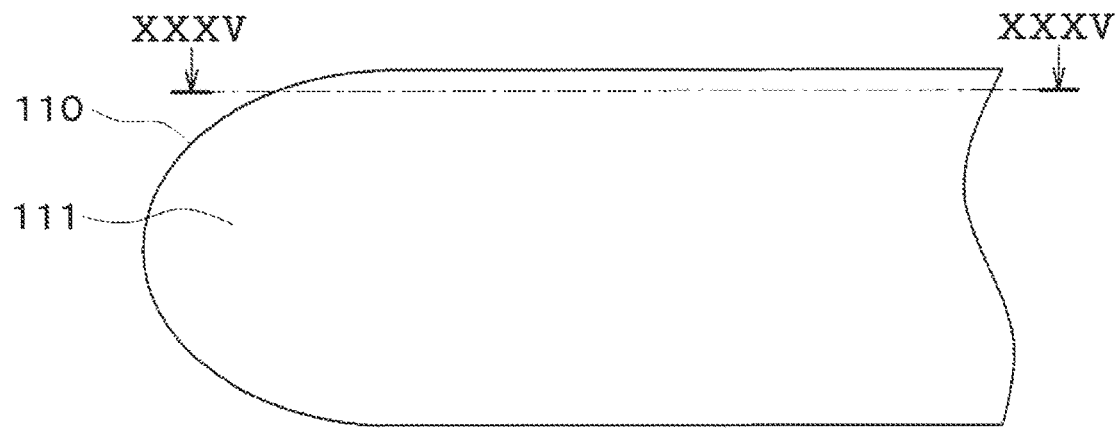
FIG. 34 is a plan view of a soil sensor according to a twentieth embodiment.
Figure 35:
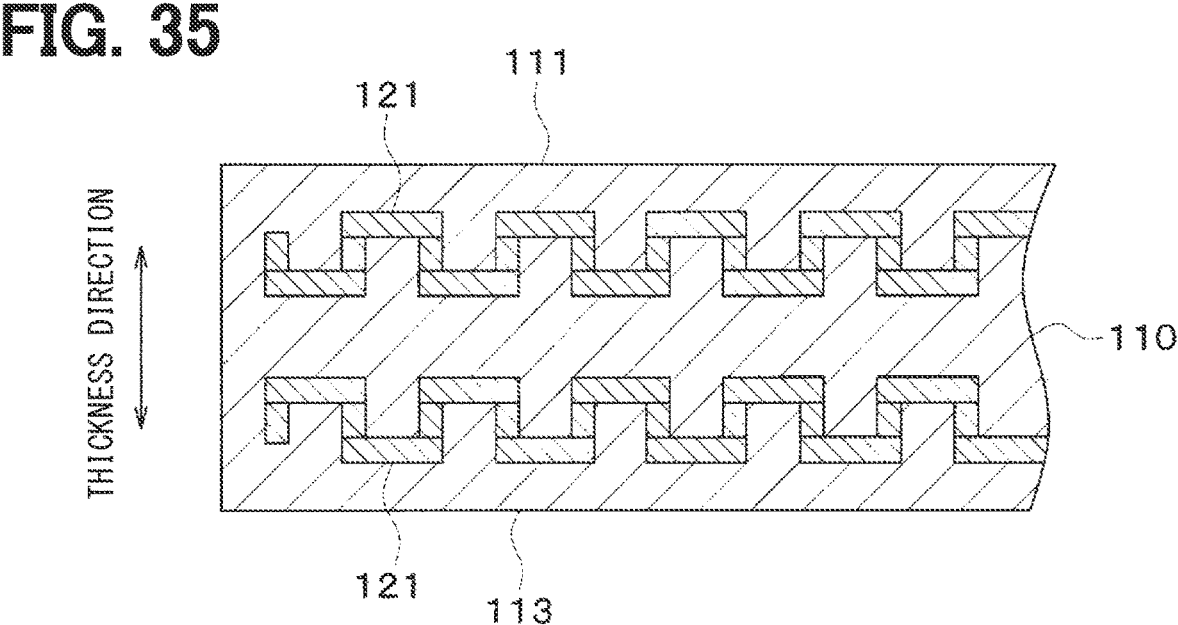
FIG. 35 is a cross-sectional view taken along line XXXV-XXXV of FIG. 34.

In the present embodiment, the description primarily focuses on the portions that differ from the above embodiments. As illustrated in FIGS. 34 and 35, the first signal line 121 is formed as wavelike wiring patterns whose amplitude changes in the thickness direction perpendicular to the one surface 111 of the base 110. In FIGS. 34 and 35, the illustration of the second to fifth detection units 130 to 160 is omitted.

The first signal line 121 is configured, for example, by electrically connecting intermittent wiring patterns at four levels formed inside the base 110, in the thickness direction, with vias or the like. In the first signal line 121, regarding the side of the one surface 111 of the base 110, two levels on the side of the one surface 111 of the base 110 are electrically connected in the thickness direction with vias or the like. In the first signal line 121, regarding the side of the other surface 113 of the base 110, two levels on the side of the other surface 113 of the base 110 are electrically connected in the thickness direction with vias or the like. The first GND line 122 is also formed as wavelike wiring patterns similar to those of the first signal line 121.

The above configuration allows the first signal line 121 and the first GND line 122 to be lengthened. The sensitivity of the first detection unit 120 can be therefore enhanced, similarly to the second embodiment.

Of course, combination can be made with other embodiments. For example, a wavelike wiring pattern may also be formed in the folded wiring pattern on the one surface 111 of the base 110 illustrated in FIG. 9 such that the wiring pattern has an amplitude changing in the thickness direction of the base 110. Similarly, the wiring pattern according to the present embodiment can also be applied to the respective wiring patterns illustrated in FIGS. 12 to 33.

As a modification, a part of the first signal line 121 may be arranged on each of the one surface 111 and the other surface 113 of the base 110. Similarly, a part of the first signal line 121 may be arranged on each of the one surface 111 and the other surface 113 of the base 110.

As another modification, the first signal line 121 and the first GND line 122 may not be arranged on the side of the other surface 113 of the base 110. When an arrangement of the first signal line 121 and the first GND line 122 is made at a plurality of levels, each of the branched patterns is formed as a wavelike wiring pattern whose amplitude changes in the thickness direction.

The present disclosure is not limited to the embodiments described above, and can be variously modified as follows without departing from the gist of the present disclosure. For example, the above embodiments can be appropriately combined. When the formation of the wiring pattern is made on each of the one surface 111 and the other surface 113 of the base 110, the wiring pattern on the one surface 111 and the wiring pattern on the other surface 113 are desirably the same.

The soil sensor 100 may be configured to measure the water content and the water potential among the physical quantities. Alternatively, the soil sensor 100 may be configured to measure the water content, the water potential, and the electric conductivity among the physical quantities. Alternatively, the soil sensor 100 may be configured to measure the water content, the water potential, the electric conductivity, and the temperature among the physical quantities. Alternatively, the soil sensor 100 may be configured to measure the water content, the water potential, the electric conductivity, the temperature, and the pH among the physical quantities. Alternatively, the soil sensor 100 may be configured to measure the water content, the water potential, the electric conductivity, the temperature, and the redox potential among the physical quantities. Alternatively, the soil sensor 100 may be configured to measure the water content, the water potential, the electric conductivity, the pH, and the redox potential among the physical quantities. Alternatively, the soil sensor 100 may be configured to measure the water content, the water potential, the electric conductivity, and the redox potential among the physical quantities. Alternatively, the soil sensor 100 may be configured to measure the water content, the water potential, and the temperature among the physical quantities. Alternatively, the soil sensor 100 may be configured to measure the water content, the water potential, the temperature, the pH, and the redox potential among the physical quantities. Alternatively, the soil sensor 100 may be configured to measure the water content, the water potential, the temperature, and the redox potential among the physical quantities. Alternatively, the soil sensor 100 may be configured to measure the water content, the water potential, and the pH among the physical quantities. Alternatively, the soil sensor 100 may be configured to measure the water content, the water potential, the pH, and the redox potential among the physical quantities. Alternatively, the soil sensor 100 may be configured to measure the water content, the water potential, and the redox potential among the physical quantities.

The soil sensor 100 may be configured to measure the electric conductivity and the water potential among the physical quantities. Alternatively, the soil sensor 100 may be configured to measure the electric conductivity, the water potential, and the water content among the physical quantities. Alternatively, the soil sensor 100 may be configured to measure the electric conductivity, the water potential, the water content, and the temperature among the physical quantities. Alternatively, the soil sensor 100 may be configured to measure the electric conductivity, the water potential, the water content, the temperature, and the pH among the physical quantities. Alternatively, the soil sensor 100 may be configured to measure the electric conductivity, the water potential, the water content, the temperature, the pH, and the redox potential among the physical quantities. Alternatively, the soil sensor 100 may be configured to measure the electric conductivity, the water potential, the water content, the temperature, and the redox potential among the physical quantities. Alternatively, the soil sensor 100 may be configured to measure the electric conductivity, the water potential, the water content, the pH, and the redox potential among the physical quantities. Alternatively, the soil sensor 100 may be configured to measure the electric conductivity, the water potential, the water content, and the redox potential among the physical quantities. Alternatively, the soil sensor 100 may be configured to measure the electric conductivity, the water potential, and the temperature among the physical quantities. Alternatively, the soil sensor 100 may be configured to measure the electric conductivity, the water potential, the temperature, the pH, and the redox potential among the physical quantities. Alternatively, the soil sensor 100 may be configured to measure the electric conductivity, the water potential, the temperature, and the redox potential among the physical quantities. Alternatively, the soil sensor 100 may be configured to measure the electric conductivity, the water potential, and the pH among the physical quantities. Alternatively, the soil sensor 100 may be configured to measure the electric conductivity, the water potential, the pH, and the redox potential among the physical quantities. Alternatively, the soil sensor 100 may be configured to measure the electric conductivity, the water potential, and the redox potential among the physical quantities.

The soil sensor 100 may be configured to measure the water content and the electric conductivity among the physical quantities. Of course, similarly to the above, appropriate combination for the configuration of the soil sensor 100 may be made among each configuration configured to measure a corresponding one of the water potential, the temperature, the pH, and the redox potential, based on the configuration configured to measure the water content and the electric conductivity.

The soil sensor 100 may be configured to measure the electric conductivity and the water potential among the physical quantities. Alternatively, the soil sensor 100 may be configured to measure the electric conductivity, the water potential, and the water content among the physical quantities. Alternatively, the soil sensor 100 may be configured to measure the electric conductivity, the water potential, the water content, and the temperature among the physical quantities. Alternatively, the soil sensor 100 may be configured to measure the electric conductivity, the water potential, the water content, the temperature, and the pH among the physical quantities. Alternatively, the soil sensor 100 may be configured to measure the electric conductivity, the water potential, the water content, the temperature, and the redox potential among the physical quantities. Alternatively, the soil sensor 100 may be configured to measure the electric conductivity, the water potential, the water content, the pH, and the redox potential among the physical quantities. Alternatively, the soil sensor 100 may be configured to measure the electric conductivity, the water potential, the water content, and the redox potential among the physical quantities. Alternatively, the soil sensor 100 may be configured to measure the electric conductivity, the water potential, and the temperature among the physical quantities.

Alternatively, the soil sensor 100 may be configured to measure the electric conductivity, the water potential, the temperature, the pH, and the redox potential among the physical quantities. Alternatively, the soil sensor 100 may be configured to measure the electric conductivity, the water potential, the temperature, and the redox potential among the physical quantities. Alternatively, the soil sensor 100 may be configured to measure the electric conductivity, the water potential, and the pH among the physical quantities. Alternatively, the soil sensor 100 may be configured to measure the electric conductivity, the water potential, the pH, and the redox potential among the physical quantities. Alternatively, the soil sensor 100 may be configured to measure the electric conductivity, the water potential, and the redox potential among the physical quantities.

The soil sensor 100 may be configured to measure the electric conductivity and the water content among the physical quantities. Alternatively, the soil sensor 100 may be configured to measure the electric conductivity, the water content, and the water potential among the physical quantities. Alternatively, the soil sensor 100 may be configured to measure the electric conductivity, the water content, the water potential, and the temperature among the physical quantities. Alternatively, the soil sensor 100 may be configured to measure the electric conductivity, the water content, the water potential, the temperature, and the pH among the physical quantities. Alternatively, the soil sensor 100 may be configured to measure the electric conductivity, the water content, the water potential, the temperature, the pH, and the redox potential among the physical quantities. Alternatively, the soil sensor 100 may be configured to measure the electric conductivity, the water content, the water potential, the temperature, and the redox potential among the physical quantities. Alternatively, the soil sensor 100 may be configured to measure the electric conductivity, the water content, the water potential, the pH, and the redox potential among the physical quantities. Alternatively, the soil sensor 100 may be configured to measure the electric conductivity, the water content, the water potential, and the redox potential among the physical quantities. Alternatively, the soil sensor 100 may be configured to measure the electric conductivity, the water content, and the temperature among the physical quantities. Alternatively, the soil sensor 100 may be configured to measure the electric conductivity, the water content, the temperature, the pH, and the redox potential among the physical quantities. Alternatively, the soil sensor 100 may be configured to measure the electric conductivity, the water content, the temperature, and the redox potential among the physical quantities. Alternatively, the soil sensor 100 may be configured to measure the electric conductivity, the water content, and the pH among the physical quantities. Alternatively, the soil sensor 100 may be configured to measure the electric conductivity, the water content, the pH, and the redox potential among the physical quantities. Alternatively, the soil sensor 100 may be configured to measure the electric conductivity, the water content, and the redox potential among the physical quantities.

The soil sensor 100 may be configured to measure the water potential and the water content among the physical quantities. Of course, similarly to the above, appropriate combination for the configuration of the soil sensor 100 may be made among each configuration configured to measure a corresponding one of the electric conductivity, the temperature, the pH, and the redox potential, based on the configuration configured to measure the water potential and the water content.

Although the present disclosure has been described in accordance with the embodiments, it is to be understood that the present disclosure is not limited to the embodiments and structures. The present disclosure also includes various modifications and variations within the scope of equivalents. Various combinations or forms, or other combinations or forms, in which only one element, one or more elements, or one or less elements are added to the various combinations or forms, are also within the scope and idea of the present disclosure.

What is claimed is:

1. A soil sensor comprising:
    a base having an installation surface;
    a first detection unit including a first signal line and a first GND line arranged on the base;
    a second detection unit including a second signal line and a second GND line arranged on the installation surface of the base, and a ceramic body, the second signal line having one end portion that is one electrode with respect to the ceramic body, the second GND line having one end portion that is the other electrode with respect to the ceramic body; and
    a circuit unit configured to
    input a frequency signal between one end portion of the first signal line and one end portion of the first GND line,
    obtain water content of soil, in which the base is arranged, based on a propagation time taken for the frequency signal to reach the other end portion of the first signal line, and
    measure a water potential of the soil based on capacitance between the one end portion of the second signal line and the one end portion of the second GND line, the capacitance being changed by water entering the ceramic body from the soil, wherein
    the first signal line has a circular wiring pattern, when being projected on the installation surface of the base,
    the first GND line is arranged to be spaced from the first signal line, and has a wiring pattern, when being projected on the installation surface of the base, within a region surrounded by the wiring pattern of the first signal line projected on the installation surface, and
    the second detection unit is arranged within a region surrounded by the wiring pattern of the first GND line projected on the installation surface of the base.

2. The soil sensor according to claim 1, wherein the circuit unit is configured to obtain electric conductivity of the soil, based on steepness of a slope of a rise of the frequency signal reaching the other end portion of the first signal line.

3. The soil sensor according to claim 1, further comprising a third detection unit arranged on the installation surface of the base within a region surrounded by the first GND line projected on the installation surface, so as to detect a temperature of the soil, wherein
    the circuit unit is configured to obtain the temperature of the soil, based on a detection result from the third detection unit.

4. The soil sensor according to claim 1, further comprising a fourth detection unit arranged on the installation surface of the base within a region surrounded by the first GND line projected on the installation surface, so as to detect a potential difference between a pair of electrodes, the potential difference being caused along with adhesion of the water contained in the soil to one of the pair of electrodes, wherein
    the circuit unit is configured to obtain pH of the soil, based on the potential difference between the pair of electrodes.

5. The soil sensor according to claim 1, further comprising a fifth detection unit arranged on the installation surface of the base within a region surrounded by the first GND line projected on the installation surface, so as to detect a potential difference between a detection electrode and a reference electrode, the potential difference being caused along with adhesion of the water contained in the soil to the detection electrode, wherein
the circuit unit is configured to obtain a redox potential of the soil, based on the potential difference between the detection electrode and the reference electrode.

6. The soil sensor according to claim 1, wherein the first detection unit is one of a plurality of first detection units installed to the base to obtain the water content at different positions in a gravity direction.

7. A soil sensor comprising:
a base having an installation surface;
a first detection unit including a first signal line and a first GND line arranged on the base;
a second detection unit including a second signal line and a second GND line arranged on the installation surface of the base, and a ceramic body, the second signal line having one end portion that is one electrode with respect to the ceramic body, the second GND line having one end portion that is the other electrode with respect to the ceramic body; and
a circuit unit configured to
input a frequency signal between one end portion of the first signal line and one end portion of the first GND line,
obtain electric conductivity of soil, in which the base is arranged, based on steepness of a slope of a rise of the frequency signal reaching the other end portion of the first signal line, and
measure a water potential of the soil based on capacitance between the one end portion of the second signal line and the one end portion of the second GND line, the capacitance being changed by water entering the ceramic body from the soil, wherein
the first signal line has a circular wiring pattern, when being projected on the installation surface of the base,
the first GND line is arranged to be spaced from the first signal line, and has a wiring pattern, when being projected on the installation surface of the base, within a region surrounded by the wiring pattern of the first signal line projected on the installation surface, and
the second detection unit is arranged within a region surrounded by the wiring pattern of the first GND line projected on the installation surface of the base.

8. The soil sensor according to claim 7, wherein the circuit unit is configured to obtain water content of the soil, based on a propagation time taken for the frequency signal to reach the other end portion of the first signal line.

9. The soil sensor according to claim 7, further comprising a third detection unit arranged on the installation surface of the base within a region surrounded by the first GND line projected on the installation surface, so as to detect a temperature of the soil, wherein
the circuit unit is configured to obtain the temperature of the soil, based on a detection result from the third detection unit.

10. The soil sensor according to claim 7, further comprising a fourth detection unit arranged on the installation surface of the base within a region surrounded by the first GND line projected on the installation surface, so as to detect a potential difference between a pair of electrodes, the potential difference being caused along with adhesion of the water contained in the soil to one of the pair of electrodes, wherein
the circuit unit is configured to obtain pH of the soil, based on the potential difference between the pair of electrodes.

11. The soil sensor according to claim 7, further comprising a fifth detection unit arranged on the installation surface of the base within a region surrounded by the first GND line projected on the installation surface, so as to detect a potential difference between a detection electrode and a reference electrode, the potential difference being caused along with adhesion of the water contained in the soil to the detection electrode, wherein
the circuit unit is configured to obtain a redox potential of the soil, based on the potential difference between the detection electrode and the reference electrode.

12. The soil sensor according to claim 7, wherein the first detection unit is one of a plurality of first detection units installed to the base to obtain the electric conductivity at different positions in a gravity direction.

13. The soil sensor according to claim 1, wherein the second detection unit is one of a plurality of second detection units installed to the installation surface of the base to obtain the water potential at different positions in a gravity direction.

14. The soil sensor according to claim 1, wherein
the base is a substrate, and
the installation surface is one surface of the substrate.

15. The soil sensor according to claim 1, wherein
the base is a substrate,
the installation surface has one surface of the substrate and the other surface of the substrate opposite to the one surface, and
the first detection unit is arranged on the one surface of the substrate and the other surface of the substrate.

16. The soil sensor according to claim 1, wherein
the wiring pattern of the first signal line projected on the installation surface of the base includes a first straight portion, a second straight portion arranged in parallel with the first straight portion, and a connection portion connecting the first straight portion and the second straight portion,
a side of the first straight portion opposite to the connection portion corresponds to the one end portion of the first signal line,
a side of the second straight portion opposite to the connection portion corresponds to the other end portion of the first signal line, and
the connection portion is a wiring pattern folded toward a wiring pattern of the first straight portion corresponding to the one end portion of the first signal line and a wiring pattern of the second straight portion corresponding to the other end portion of the first signal line.

17. The soil sensor according to claim 1, wherein
the wiring pattern of the first signal line projected on the installation surface of the base includes a first straight portion, a second straight portion arranged in parallel with the first straight portion, and a connection portion connecting the first straight portion and the second straight portion, and
one of the first straight portion and the second straight portion includes a wiring pattern portion having a meandering pattern.

18. The soil sensor according to claim 1, wherein
the wiring pattern of the first signal line projected on the installation surface of the base includes a first straight portion, a second straight portion arranged in parallel with the first straight portion, and a connection portion connecting the first straight portion and the second straight portion, the first straight portion includes a first wiring pattern portion having a meandering pattern, and the second straight portion includes a second wiring pattern portion having a meandering pattern.

19. The soil sensor according to claim 1, wherein the base and the circuit unit are integrated, and are arranged along a direction perpendicular to a gravity direction.

20. The soil sensor according to claim 1, wherein the base and the circuit unit are integrated, and the circuit unit is arranged to be positioned on an upper side of the base in a gravity direction.

21. The soil sensor according to claim 1, wherein the one end portion of the second signal line and the one end portion of the second GND line are arranged on the installation surface of the base, the ceramic body is arranged above the one end portion of the second signal line and the one end portion of the second GND line, and the one end portion of the second GND line is arranged to be spaced from the one end portion of the second signal line, and is a wiring pattern surrounding the one end portion of the second signal line.

22. The soil sensor according to claim 21, wherein the ceramic body has an obverse surface and a reverse surface, and the reverse surface is arranged on a side of the one end portion of the second signal line and the one end portion of the second GND line, the second detection unit includes a metal body arranged on the obverse surface of the ceramic body and electrically connected to the second GND line, and the metal body is the other electrode with respect to the ceramic body.

23. The soil sensor according to claim 21, wherein the ceramic body has an obverse surface and a reverse surface, and the reverse surface is arranged on a side of the one end portion of the second signal line and the one end portion of the second GND line, the second detection unit includes a metal body arranged on the obverse surface of the ceramic body and electrically connected to the second signal line, and the metal body is the one electrode with respect to the ceramic body.

24. The soil sensor according to claim 1, wherein the one end portion of the second signal line is arranged on the installation surface of the base, the ceramic body has an obverse surface, a reverse surface, and a side surface, and the reverse surface is positioned above the one end portion of the second signal line, a part of the second GND line is arranged on the side surface of the ceramic body, and the one end portion of the second GND line is arranged on the obverse surface of the ceramic body.

25. The soil sensor according to claim 1, wherein the one end portion of the second GND line is arranged on the installation surface of the base, the ceramic body has an obverse surface, a reverse surface, and a side surface, and the reverse surface is positioned above the one end portion of the second GND line, a part of the second signal line is arranged on the side surface of the ceramic body, and the one end portion of the second signal line is arranged on the obverse surface of the ceramic body.

26. The soil sensor according to claim 1, wherein the one end portion of the second signal line is arranged on the installation surface of the base, the ceramic body has an obverse surface, a reverse surface, and a side surface, and the reverse surface is positioned above the one end portion of the second signal line, and the one end portion of the second GND line is arranged on the side surface of the ceramic body.

27. The soil sensor according to claim 1, wherein the one end portion of the second GND line is arranged on the installation surface of the base, the ceramic body has an obverse surface, a reverse surface, and a side surface, and the reverse surface is positioned above the one end portion of the second GND line, and the one end portion of the second signal line is arranged on the side surface of the ceramic body.

28. The soil sensor according to claim 1, wherein the one end portion of the second signal line is arranged on the installation surface of the base, the ceramic body has an obverse surface, a reverse surface, and a side surface, and the reverse surface is positioned above the one end portion of the second signal line, and the one end portion of the second GND line is arranged on the obverse surface and the side surface of the ceramic body.

29. The soil sensor according to claim 1, wherein the one end portion of the second GND line is arranged on the installation surface of the base, the ceramic body has an obverse surface, a reverse surface, and a side surface, and the reverse surface is positioned above the one end portion of the second GND line, and the one end portion of the second signal line is arranged on the obverse surface and the side surface of the ceramic body.

30. The soil sensor according to claim 1, wherein the first signal line has layer-like wiring patterns that extend along the installation surface of the base, and that are in different positions in a thickness direction defined with respect to the installation surface of the base, and the first GND line has layer-like wiring patterns that extend along the installation surface of the base, and that are in different positions in a thickness direction defined with respect to the installation surface of the base.

31. The soil sensor according to claim 1, wherein the first signal line and the first GND line are arranged at different depths defined with respect to the installation surface, in a thickness direction perpendicular to the installation surface of the base.

32. The soil sensor according to claim 1, wherein the first signal line and the first GND line are wavelike wiring patterns whose amplitudes change in a thickness direction perpendicular to the installation surface of the base.

* * * * *